(12) United States Patent
Lowrey et al.

(10) Patent No.: US 12,359,230 B2
(45) Date of Patent: Jul. 15, 2025

(54) MICROBIAL OILS WITH HIGH LEVELS OF OMEGA-3 FATTY ACIDS

(71) Applicant: MARA Renewables Corporation, Dartmouth (CA)

(72) Inventors: Joshua Lowrey, Dartmouth (CA); Zhiyong Sun, Dartmouth (CA); Roberto E. Armenta, Dartmouth (CA); Denise Muise, Dartmouth (CA)

(73) Assignee: MARA Renewables Corporation, Dartmouth (CA)

( * ) Notice: Subject to any disclaimer, the term of this patent is extended or adjusted under 35 U.S.C. 154(b) by 0 days.

(21) Appl. No.: 17/221,810

(22) Filed: Apr. 4, 2021

(65) Prior Publication Data

US 2021/0310032 A1    Oct. 7, 2021

Related U.S. Application Data

(60) Provisional application No. 63/005,054, filed on Apr. 3, 2020.

(51) Int. Cl.
*C12P 7/6434* (2022.01)
*C12P 7/6427* (2022.01)

(52) U.S. Cl.
CPC ........... *C12P 7/6434* (2022.01); *C12P 7/6427* (2013.01)

(58) Field of Classification Search
CPC ..... C12P 7/6427; C12P 7/6434; C12P 7/6463; C12P 7/6472; C12P 7/6432; C12N 1/12; C12R 2001/89
See application file for complete search history.

(56) References Cited

U.S. PATENT DOCUMENTS

| 5,130,242 A | 7/1992 | Barclay |
| 5,374,657 A | 12/1994 | Kyle |
| 5,397,591 A | 3/1995 | Kyle et al. |
| 5,407,957 A | 4/1995 | Kyle et al. |

(Continued)

FOREIGN PATENT DOCUMENTS

| CA | 3112621 | 3/2020 |
| CN | 101252844 A | 8/2008 |

(Continued)

OTHER PUBLICATIONS

Gao, Mang, et al. "Isolation and characterization of Aurantiochytrium species: high docosahexaenoic acid (DHA) production by the newly isolated microalga, *Aurantiochytrium* sp. SD116." Journal of oleo science 62.3 (2013): 143-151. (Year: 2013).*

(Continued)

*Primary Examiner* — Louise W Humphrey
*Assistant Examiner* — Candice Lee Swift
(74) *Attorney, Agent, or Firm* — Kilpatrick Townsend & Stockton LLP (57) ABSTRACT

Provided herein are microbial oils and methods of making and using microbial oils with high levels of omega-3 fatty acids. Specifically, provided is a microbial oil comprising at least 85% total fatty acids, wherein the total fatty acids comprise at least 50% DHA. Also provided is a method of making a biomass comprising culturing an oil-producing microorganism in a culture medium comprising a fatty acid synthesis inhibitor, wherein the biomass comprises at least 500 mg/g oil.

11 Claims, 4 Drawing Sheets

(56) References Cited

U.S. PATENT DOCUMENTS

| | | |
|---|---|---|
| 5,476,787 A | 12/1995 | Yokoyama et al. |
| 5,492,938 A | 2/1996 | Kyle et al. |
| 6,166,231 A | 12/2000 | Hoeksema |
| 6,201,145 B1 | 3/2001 | Fan |
| 6,270,828 B1 | 8/2001 | DeBonte et al. |
| 6,399,803 B1 | 6/2002 | Corley et al. |
| 6,582,941 B1 | 6/2003 | Yokochi et al. |
| 8,148,559 B1 | 4/2012 | Walker et al. |
| 8,207,363 B2 | 6/2012 | Apt et al. |
| 9,023,616 B2 | 5/2015 | Radianingtyas et al. |
| 10,362,794 B2 | 7/2019 | Apt et al. |
| 10,392,578 B2 | 8/2019 | Cherinko et al. |
| 10,757,959 B2 | 9/2020 | Apt et al. |
| 11,198,891 B2 | 12/2021 | Ugalde et al. |
| 11,525,103 B2 | 12/2022 | Sekiguchi et al. |
| 2001/0025114 A1 | 9/2001 | Bijl et al. |
| 2002/0001833 A1 | 1/2002 | Ruecker et al. |
| 2003/0060509 A1 | 3/2003 | Elswyk |
| 2003/0143659 A1 | 7/2003 | Bijl et al. |
| 2003/0161864 A1 | 8/2003 | Tanaka et al. |
| 2004/0092590 A1 | 5/2004 | Arterburn et al. |
| 2004/0161831 A1 | 8/2004 | Komazawa et al. |
| 2005/0027004 A1 | 2/2005 | Kyle et al. |
| 2005/0129831 A1 | 6/2005 | Fabritius |
| 2005/0170479 A1 | 8/2005 | Weaver et al. |
| 2005/0220958 A1 | 10/2005 | Schaap et al. |
| 2005/0273885 A1 | 12/2005 | Singh et al. |
| 2006/0094089 A1 | 5/2006 | Barclay |
| 2006/0099693 A1 | 5/2006 | Kobzeff et al. |
| 2007/0003686 A1 | 1/2007 | Fichtali et al. |
| 2007/0104856 A1 | 5/2007 | Standal et al. |
| 2007/0112071 A1 | 5/2007 | Bryhn et al. |
| 2007/0141222 A1 | 6/2007 | Binder et al. |
| 2007/0184090 A1 | 8/2007 | Van Waterschoot et al. |
| 2007/0243307 A1 | 10/2007 | Abril et al. |
| 2007/0248586 A1 | 10/2007 | Arterburn et al. |
| 2008/0038800 A1 | 2/2008 | Ruecker et al. |
| 2008/0175975 A1 | 7/2008 | Fabritius |
| 2009/0064567 A1 | 3/2009 | Lippmeier et al. |
| 2009/0118525 A1 | 5/2009 | Wang |
| 2010/0285105 A1* | 11/2010 | Radianingtyas ........ A61P 39/06 426/643 |
| 2010/0298435 A1 | 11/2010 | Abril et al. |
| 2015/0361461 A1 | 12/2015 | Chen et al. |
| 2018/0179560 A1* | 6/2018 | Ugalde ..................... C12N 1/10 |
| 2018/0273877 A1 | 9/2018 | Sekiguchi et al. |
| 2022/0041953 A1 | 2/2022 | Bourles et al. |
| 2022/0042054 A1* | 2/2022 | Godart .................. C12P 7/6472 |

FOREIGN PATENT DOCUMENTS

| | | | |
|---|---|---|---|
| CN | 101981201 A | | 2/2011 |
| CN | 106834125 A | | 6/2017 |
| CN | 107075538 A | | 8/2017 |
| EP | 0707487 A1 | | 4/1996 |
| EP | 0831805 A1 | | 4/1998 |
| EP | 1178118 A1 | | 2/2002 |
| EP | 1506996 A2 | | 2/2005 |
| EP | 2337857 A1 | | 6/2011 |
| EP | 2391361 A1 | | 12/2011 |
| EP | 2405895 A1 | | 1/2012 |
| EP | 3385359 | | 10/2018 |
| EP | 2576801 B1 | | 10/2019 |
| EP | 2921155 B1 | | 1/2020 |
| EP | 3530740 B1 | | 7/2021 |
| GB | 2379166 A | | 3/2003 |
| JP | H08163990 A | | 6/1996 |
| JP | H0975000 A | | 3/1997 |
| JP | H1072590 A | | 3/1998 |
| JP | 2000060587 A | | 2/2000 |
| JP | 2001309797 A | | 11/2001 |
| JP | 2010511377 A | | 4/2010 |
| WO | 9428891 A1 | | 12/1994 |
| WO | 9428913 A1 | | 12/1994 |
| WO | 9737032 A2 | | 10/1997 |
| WO | 0149282 A2 | | 7/2001 |
| WO | 0153512 A1 | | 7/2001 |
| WO | 0210423 A2 | | 2/2002 |
| WO | 03092628 A2 | | 11/2003 |
| WO | 2004028469 A2 | | 4/2004 |
| WO | 2005083093 A2 | | 9/2005 |
| WO | 2007005725 A2 | | 1/2007 |
| WO | 2008129358 A2 | | 10/2008 |
| WO | 2008155410 A1 | | 12/2008 |
| WO | 2009029793 A1 | | 3/2009 |
| WO | 2009040676 A2 | | 4/2009 |
| WO | 2010107415 A1 | | 9/2010 |
| WO | 2011090493 A1 | | 7/2011 |
| WO | 2011153246 A2 | | 12/2011 |
| WO | 2015092546 A1 | | 6/2015 |
| WO | 2015179844 | | 11/2015 |
| WO | 2015179844 A2 | | 11/2015 |
| WO | 2017094804 A1 | | 6/2017 |
| WO | 2018116093 A1 | | 6/2018 |
| WO | 2020053372 A1 | | 3/2020 |

OTHER PUBLICATIONS

Harvard Health; https://www.health.harvard.edu/heart-health/understanding-triglycerides#:~:text=Triglycerides%20are%20the%20most%20common,reassembled%20to%20create%20triglyceride%20particles.; accessed Feb. 2, 2023 (Year: 2020).*

Chen, Wei, et al. "Transcriptome analysis reveals that up-regulation of the fatty acid synthase gene promotes the accumulation of docosahexaenoic acid in *Schizochytrium* sp. S056 when glycerol is used." Algal research 15 (2016): 83-92. (Year: 2016).*

Ratledge, Colin. "Single cell oils for the 21st century." Single cell oils. AOCS Press, 2010. 3-26. (Year: 2010).*

Yano, Yutaka, et al. "Production of docosahexaenoic acid by marine bacteria isolated from deep sea fish." Lipids 29.7 (1994): 527-528. (Year: 1994).*

Hamamoto, Tetsuo, et al. "Characteristic presence of polyunsaturated fatty acids in marine psychrophilic vibrios." FEMS microbiology letters 129.1 (1995): 51-56. (Year: 1995).*

Heggeset, Tonje MB, et al. "Lipid and DHA-production in *Aurantiochytrium* sp.-responses to nitrogen starvation and oxygen limitation revealed by analyses of production kinetics and global transcriptomes." Scientific reports 9.1 (2019): 19470. (Year: 2019).*

Sasaki K, Geribaldi-Doldán N, Wu Q, Davies J, Szele FG, Isoda H. Microalgae *Aurantiochytrium* Sp. Increases Neurogenesis and Improves Spatial Learning and Memory in Senescence-Accelerated Mouse-Prone 8 Mice. Front Cell Dev Biol. Feb. 9, 2021;8: 600575. (Year: 2021).*

Armenta, R.E., et al., 2006, "Critical Assessment of Various Techniques for the Extraction of Carotenoids and Co-enzyme Q10 from the Thraustochytrid Strain ONC-T18", J. Agric. Food Chem. 54, 9752-9758.

Bonilla-Mendez and Hoyos-Concha, Corpoica Cienc Tecnol Agropecuaria, Mosquera (Colombia), 19(3):645-668 (2018).

Chaung, K.C., et al., "Effect of culture conditions on growth, lipid content, and fatty acid composition of Aurantiochytrium mangrovei strain BL10", AMB Express, 2(1), 2012, p. 42.

Chen et al., "Molecular mechanisms of the coordination between astaxanthin and fatty acid biosynthesis in Haematococcus pluvialis (Chlorophyceae)", The Plant Journal, 81, 2014, pp. 95-107.

Chen, W., et al., "Transcriptome analysis reveals that up-regulation of the fatty acid synthase gene promotes the accumulation of docosahexaenoic acid in *Schizochytrium* sp. S056 when glycerol is used", Algal research, 15, 2016, pp. 83-92.

Giner-Robles et al., "fabH deletion increases DHA production in *Escherichia coli* expressing Pfa genes", Microbial Cell Factories, 2018, 17:88.

Hauvermale, A., et al., 2006. "Fatty acid production in *Schizochytrium* sp.: Involvement of a polyunsaturated fatty acid synthase and a type I fatty acid synthase", Lipids, 41(8), pp. 739-747.

Lian et al., "Increase of docosahexaenoic acid production by *Schizochytrium* sp. through mutagenesis and enzyme assay", Appl Biochem Biotechnol, 162:935-941 (2010).

(56) References Cited

OTHER PUBLICATIONS

Morita et al., "Enhancement of Polyunsaturated Fatty Acid Production by Cerulenin Treatment in Polyunsaturated Fatty Acid-producing Bacteria", Biotechnology Letters , vol. 27, No. 6, Mar. 2005, pp. 389-393.
Ratledge, C., 200, "Fatty acid biosynthesis in microorganisms being used for Single Cell Oil production", Biochimie, Recent advances in lipid metabolism and related disorders 86, 807-815. https://doi.org/10.1016/j.biochi.2004.09.017.
Sun et al., 2019, "Light induces carotenoids accumulation in a heterotrophic docosahexaenoic acid producing microalga, *Crypthecodinium* sp. Bioresource Technology", 276 pp. 177-182.
Zhang, J., 2011, "The Diversity and Biotechnological Application of Marine Microbes Producing Omega-3 Fatty Acids. School of Marine Science and Technology", Newcastle University. Thesis.
Zhao, X., Qiu, X., 2018. Analysis of the biosynthetic process of fatty acids in Thraustochytrium. Biochimie 144, 108-114. https://doi.org/10.1016/j.biochi.2017.10.024.
Application No. PCT/IB2021/052801 , International Search Report and Written Opinion, Mailed On Jun. 14, 2021, 9 pages.
PCT/IB2021/052801 , "International Preliminary Report on Patentability", Oct. 13, 2022, 8 pages.
Liu et al., "Comparative transcriptomic analysis uncovers genes responsible for the DHA enhancement in the mutant *Aurantiochytrium* sp.", Microorganisms 8.4 (2020): 529, 19 pages.
Advisory Committee on Novel Foods and Processes, Mara Renewables Corporation, Oct. 2017, 9 pages.
Application for Approval of a Novel Food: DHA-Rich Algal Oil from *Schizochytrium* sp. T18, Mara Renewables Corporation, Nov. 2016, 39 pages.
Carbohydrase Mix, Available Online at: https://www.ncbe.reading.ac.uk/carbohydrase-mix/, 4 pages.
Citation in opposition procedure-034, Untitled Report, pp. 1-6.
Curriculum Vitae of Dr. Jonathan Curtis, Exhibit 1004, 30 pages.
Curriculum Vitae of Peter David Nichols, pp. 1-114.
Declaration of Dr. Curtis, Exhibit 103, Aug. 22, 2023, 111 pages.
Declaration of Dr. Jonathan Curtis, Exhibit 1003, Nov. 17, 2023, 124 pages.
Declaration of Dr. Jonathan Curtis, Exhibit 1003, Jul. 13, 2023, 126 pages.
Declaration of Dr. Ross Zirkle, Oct. 25, 2023, 15 pages.
Declaration of Mark Oxford, Oct. 24, 2023, 3 pages.
Dhasco and Arasco Oils as Sources of Long-chain Polyunsaturated Fatty Acids in Infant Formula, Technical Report Series No. 22, Jun. 2003, pp. 1-54.
GRAS Notice, (GRN) No. 677, Available Online at: http://www.fda.gov/Food/IngredientsPackagingLabeling/GRAS/NoticeInventory/default.htm, 118 pages.
Institution Decision: Denying Institution of Inter Partes Review 35 U.S.C. sec. 314, Jan. 25, 2024, 23 pages.
Microbial Oil, Wikipedia, Accessed from Internet on Apr. 24, 2022, 5 pages.
Neutrase®, Novozymes.com, 2021, 3 pages.
Novozymes, Novozymes.com, Jun. 11, 2013, 4 pages.
Omega-3 Acid Triglycerides, Dietary Supplements, May 1, 2018, pp. 1-3.
Omega-3 Refined Fish Oil 30/20TG China Manufacturer, Sinomega, Accessed from Internet on Oct. 24, 2023, 3 pages.
Omega-3-Acid Triglycerides, European Pharmacopoeia 5.0, pp. 2144-2146.
IPR202301167, "Patent Owner's Preliminary Response", Oct. 30, 2023, 72 pages.
IPR2023-01342, "Patent Owner's Preliminary Response", Nov. 30, 2023, 77 pages.
IPR2023-01342, "Decision Denying Institution of Inter Partes Review", Feb. 23, 2024, 30 pages.
Petition for Inter Partes Review of U.S. Pat. No. 10,392,578, Jul. 14, 2023, 82 pages.
Petition for Inter Partes Review of U.S. Pat. No. 10,757,959, Aug. 22, 2023, 83 pages.
Petition for Inter Partes Review of U.S. Pat. No. 8,207,363, Nov. 22, 2023, 82 pages.
Product Data Sheet, Kinomega, Oct. 25, 2023, 2 pages.
Prosecution History of the '959 Patent, 230 pages.
Prosecution History of the '578 patent (Part 1 of 2), 445 pages.
Prosecution History of the '578 patent (Part 2 of 2), 678 pages.
Regulations: Commission Implementing Regulation (EU) 2018/1032 of Jul. 20, 2018, Official Journal of the European Union, Jul. 23, 2018, 5 pages.
T18 Mara Renewables, Google Search, 2 pages.
*Thraustochytrium* sp. PTA-6245, Product Sheet, 2021, pp. 1-5.
U.S. Appl. No. 16/935,818 File History, 262 pages.
U.S. Pat. No. 8,207,363, File History, 337 pages.
Westfalia SB7-06-076 Desludger Disc Centrifuge, Aaron Equipment Company, 1 page.
Written Submission in Preparation to/during Oral Proceedings, Oct. 24, 2023, 3 pages.
U.S. Appl. No. 08/073,505, filed Jun. 9, 1993, 54 pages.
U.S. Appl. No. 10/518,146, Non-Final Office Action mailed on Aug. 7, 2007, 7 pages.
U.S. Appl. No. 60/821,084, filed Aug. 1, 2006.
Akoh et al., Food Lipids: Chemistry, Nutrition, and Biotechnology, Second Edition, Marcel Dekker Inc., 2002, 54 pages.
Arterburn et al., A Combined Subchronic (90-day) Toxicity and Neurotoxicity Study of a Single-Cell Source of Docosahexaenoic Acid Triglyceride (DHASCO oil), Food and Chemical Toxicology, vol. 38, No. 1, Jan. 2000, pp. 35-49.
Aveldano et al., Quantitative Release of Fatty Acids from Lipids by a Simple Hydrolysis Procedure, Journal of Lipid Research, vol. 24, No. 8, 1983, pp. 1101-1105.
Bajpai et al., Optimization of Production of Docosahexaenoic Acid (DHA) by Thraustochytrium Aureum ATCC 34304, Journal of the American Oil Chemists' Society, vol. 68, No. 7, Jul. 1991, pp. 509-514.
Barron et al., The Effects of Temperature on PH Measurement, A Reagecon Technical Paper, No. 2, 8 pages.
Bhatt, Transperfect Certification, TransPerfect Translations International, Inc., Apr. 1, 2022, 1 page.
Bimbo, Marine Oils, Available online at https://lipidlibrary.aocs.org/edible-oil-processing/marine-oils, Accessed from internet on Aug. 21, 2023, 21 pages.
Bowles et al., Long-Chain n-3 Polyunsaturated Fatty Acid Production by Members of the Marine Protistan Group the Thraustochytrids: Screening of Isolates and Optimisation of Docosahexaenoic Acid Production, Journal of Biotechnology, vol. 70, Nos. 1-3, Apr. 30, 1999, pp. 193-202.
Breivik, Long-Chain Omega-3 Specialty Oils, The Oily Press, vol. 21, 2007, 81 pages.
Burja et al., Isolation and Characterization of Polyunsaturated Fatty Acid Producing *Thraustochytrium* Species: Screening of Strains and Optimization of Omega-3 Production, Applied Microbiology and Biotechnology, vol. 72, No. 6, Oct. 2006, pp. 1161-1169.
Canadian Application No. 3,172,997, Office Action mailed on Jan. 30, 2024, 3 pages.
Chang et al., Odd-Chain Polyunsaturated Fatty Acids in Thraustochytrids, Phytochemistry, vol. 72. Nos. 11-12, May 2011, pp. 1460-1465.
Chinese Application No. 202180034488.8, Office Action mailed on Dec. 12, 2023, 8 pages.
Cohen et al., Single Cell Oils: Microbial and Algal Oils, Second Edition, AOCS Press, 2010, 490 pages.
Cui et al., Cofactor Spectrum Analysis of Marine Fungus SD116 in Product Synthesis, Chinese Journal of Marine Drugs, vol. 32, No. 6, 2013, pp. 27-32.
Damodaran, Fennema's Food Chemistry, Fifth Edition, CRC press, 2017, 65 pages.
Darley et al., Cell Wall Composition and Synthesis via Golgi-Directed Scale Formation in the Marine Eucaryote, Schizochytrium Aggregatum, with a Note on *Thraustochytrium* Sp, Archives of Microbiology, vol. 90, No. 2, Mar. 26, 1973, pp. 89-106.
European Application No. 09841993.0, Response from Hoyng mailed on Apr. 27, 2022, 4 pages.

(56) References Cited

OTHER PUBLICATIONS

European Application No. 11790339.3, Decision Rejecting the Opposition mailed on Oct. 28, 2022, 20 pages.
European Application No. 11790339.3, Intervention of the Assumed Infringer mailed on Mar. 17, 2023, 10 pages.
European Application No. 11790339.3, Intervention of the Assumed Infringer mailed on Apr. 9, 2023, 13 pages.
European Application No. 11790339.3, Notice of Opposition mailed on Oct. 2, 2019, 31 pages.
European Application No. 11790339.3, Reply of the Patent Proprietor to the Notice(s) of Opposition mailed on Nov. 26, 2020, 15 pages.
European Application No. 11790339.3, Reply to an Examination Report in Opposition Proceedings mailed on Sep. 5, 2023, 18 pages.
European Application No. 11790339.3, Transmittal of Decision / Summons—Opposition mailed on Dec. 18, 2023, 17 pages.
European Application No. 11790339.3, Transmittal of Decision / Summons—Opposition mailed on Jul. 11, 2022, 28 pages.
European Application No. 11790339.3, Written Submission in Preparation to/during Oral Proceedings mailed on Apr. 13, 2023, 14 pages.
European Application No. 15153638.0, Grounds for the Decision (Annex)—Opposition mailed on Oct. 28, 2022, 18 pages.
European Application No. 15153638.0, Notice of Opposition mailed on Oct. 7, 2020, pp. 1-17.
European Application No. 15153638.0, Reply of the Patent Proprietor to the Notice(s) of Opposition mailed on Mar. 1, 2021, 11 pages.
European Application No. 15153638.0, Transmittal of decision / summons—opposition mailed on Jan. 13, 2022, 14 pages.
European Application No. 15153638.0, Transmittal of decision / summons—opposition mailed on Oct. 28, 2022, 33 pages.
European Application No. 18198460.0, Declaration of Dr. Peter Nichols mailed on Sep. 21, 2023, pp. 1-21.
European Application No. 18198460.0, Grounds for the Decision mailed on Jan. 23, 2024, 20 pages.
European Application No. 18198460.0, Interlocutory Decision in Opposition Proceedings mailed on Jan. 23, 2024, 109 pages.
European Application No. 18198460.0, Intervention of the Assumed Infringer mailed on Apr. 9, 2023, 14 pages.
European Application No. 18198460.0, Notice of Intervention mailed on Mar. 23, 2023, 18 pages.
European Application No. 18198460.0, Notice of Opposition mailed on Apr. 9, 2023, 5 pages.
European Application No. 18198460.0, Notice of Opposition mailed on May 4, 2022, 50 pages.
European Application No. 18198460.0, Reply of the Patent Proprietor to the Notice(s) of opposition mailed on Jun. 9, 2022, 24 pages.
European Application No. 18198460.0, Summons to Attend Oral Proceedings mailed on Jan. 27, 2023, 20 pages.
European Application No. 18198460.0, Witness Statement of Dr. Patti Virtue mailed on Sep. 4, 2023, 4 pages.
European Application No. 18198460.0, Witness Statement of Dr. Xiao Qiu mailed on Aug. 31, 2023, 4 pages.
European Application No. 18198460.0, Written Submission in Preparation to/during Oral Proceedings mailed on Sep. 21, 2023, 69 pages.
European Application No. 20180198460, Third Party Observation mailed on Nov. 9, 2023, 4 pages.
European Application No. 18198460.0, Declaration of Dr. Jonathan Curtis mailed on Aug. 22, 2023, pp. 1-112.
Fan et al., Chapter 11. Production of High-Value Products by Marine Microalgae Thraustochytrids, In Book of Bioprocessing for Value-Added Products from Renewable Resources, New Technologies and Applications, 2007, pp. 293-323.
Fan et al., Lipid Characterization of Mangrove Thraustochytrid, Journal of Agricultural and Food Chemistry, vol. 55, No. 8, Apr. 2007, pp. 2906-2910.
Frankel, Lipid Oxidation, Second Edition, Woodhead Publishing in Food Science, Technology and Nutrition, 2023, 488 pages.

Furlan et al., Production of Docosahexaenoic Acid (DHA) from *Thraustochytrium* sp. ATCC 26185 Using Differents Nitrogen Concentrations, Boletim Do Centro De Pesquisa De Processamento De Alimentos, vol. 32, No. 1, Jul. 2014, pp. 1-10.
Gortner, An Evaluation of Micromethods for Phospholipid, Journal of Biological Chemistry, vol. 159, No. 1, Jun. 1945, pp. 97-100.
Huang et al., Profile of Polyunsaturated Fatty Acids Produced by *Thraustochytrium* Sp. KK17-3, Journal of the American Oil Chemists' Society, vol. 78, No. 6, Jun. 2001, pp. 605-610.
Humphrey, Shake Flask to Fermentor: What Have We Learned?, Biotechnology Progress, vol. 14, No. 1, 1998, pp. 3-7.
Iida et al., Improvement of Docosahexaenoic Acid Production in a Culture of Thraustochytrium Aureum by Medium Optimization, Journal of Fermentation and Bioengineering, vol. 81, Issue 1, 1996, pp. 76-78.
Jakobsen et al., Accumulation of Docosahexaenoic Acid-Rich Lipid in *Thraustochytrid aurantiochytrium* Sp. Strain T66: Effects of N and P Starvation and O2 Limitation, Applied Microbiology and Biotechnology, vol. 80, No. 2, Aug. 2008, pp. 297-306.
Jeh et al., Lipid body Formation by Thraustochytrium Aureum (ATCC 34304) in Response to Cell, Korean Journal of Chemical Engineering, vol. 25, No. 5, Jan. 9, 2009, pp. 1103-1109.
Kyle, Production and Use of a Single Cell Oil Which is Highly Enriched in Docosahexaenoic, Lipid Technology, Sep. 1996, 4 pages.
Lee-Chang et al., Docosahexaenoic Acid Is Naturally Concentrated at the sn-2 Position in Triacylglycerols of the Australian *Thraustochytrid aurantiochytrium* sp. Strain TC 20, Marine Drugs, vol. 19, No. 7, Jul. 2021, 11 pages.
Lepage et al., Improved Recovery of Fatty Acid Through Direct Transesterification without Prior Extraction or Purification, Journal of Lipid Research, vol. 25, No. 12, Dec. 1984, pp. 1391-1396.
Lewis, Characterisation and Application of Australian Thraustochytrids, Doctoral Dissertation, University of Tasmania, Jun. 2001, 188 pages.
Lewis et al., The Biotechnological Potential of Thraustochytrids, Marine Biotechnology, vol. 1, No. 6, Nov. 1999, pp. 580-587.
Maas et al., Molecular Characterization of QPX (Quahog Parasite Unknown), a Pathogen of Mercenaria Mercenaria, Journal of Shellfish Research, vol. 18, No. 2, 1999, pp. 561-567.
Marchan et al., Screening of New British Thraustochytrids Isolates for Docosahexaenoic Acid (DHA) Production, Journal of Applied Phycology, vol. 29, No. 6, Dec. 2017, pp. 2831-2843.
Medina et al., Downstream Processing of Algal Polyunsaturated Fatty Acids, Biotechnology Advances, vol. 16, Issue 3, May 1998, pp. 517-580.
Mo et al., A Simple, Reliable, and Fast Protocol for Thraustochytrid DNA Extraction, Marine Biotechnology, vol. 3, No. 2, Mar. 2001, 3 pages.
Molobela et al., Protease and Amylase Enzymes for Biofilm Removal and Degradation of Extracellular Polymeric Substances (EPS) Produced by Pseudomonas Fluorescens Bacteria, African Journal of Microbiology Research, vol. 4, No. 14, Available Online at: https://academicjournals.org/article/article1380288611_Molobela%20et%20al.pdf, Jul. 18, 2010, pp. 1515-1524.
Myher et al., Stereospecific Analysis of Triacylglycerols Rich in Long-Chain Polyunsaturated Fatty Acids, Journal of Lipids, vol. 31, No. 2, Feb. 1996, pp. 207-215.
Nakahara et al., Production of Docosahexaenoic and Docosapentaenoic Acids by *Schizochytrium* sp. Isolated from Yap Islands, Journal of the American Oil Chemists Society, vol. 73, No. 11, Nov. 1996, pp. 1421-1426.
Nelson et al., Lipid Biosynthesis, Lehninger, Principles of Biochemistry, 2008, 4 pages.
Nichols et al., New Australian Single Cell and Crop Plant Sources of Health-enhancing Long-chain Omega-3 Oils, Australasian Biotechnology vol. 13, No. 5, Oct.-Nov. 2003, pp. 26-28.
Nichols et al., Omega-3 Oils Down Under—An Update, Inform, vol. 15, No. 6, Jun. 2004, 4 pages.
Raghukumar, Thraustochytrid Marine Protists: Production of PUFAs and Other Emerging Technologies, Marine Biotechnology, vol. 10, No. 6, Dec. 2008, pp. 631-640.

(56) References Cited

OTHER PUBLICATIONS

Ratnayake et al., Preparation of Omega-3 PUFA Concentrates from Fish Oils via Urea Complexation, Lipid/Fett, vol. 90, No. 10, 1988, pp. 381-386.
Schorken et al., Lipid Biotechnology: Industrially Relevant Production Processes, European Journal of Lipid Science and Technology, vol. 111, No. 7, Jul. 17, 2009, pp. 627-645.
Shahidi et al., Omega-3 Polyunsaturated Fatty Acids and Their Health Benefits, Annual Review of Food Science and Technology, vol. 9, Mar. 25, 2018, pp. 345-381.
Taberna, Heterotrophic Cultivation of Microalgae as A Source of Docosahexaenoic Acid for Aquaculture, 2008, 203 pages.
Tanaka et al., Concentration of Docosahexaenoic Acid in Glyceride by Hydrolysis of Fish Oil with Candida Cylindracea Lipase, Journal of the American Oil Chemists' Society, vol. 69, No. 12, Dec. 1992, pp. 1210-1214.
Volkman, Sterols in Microorganisms, Applied Microbiology and Biotechnology, vol. 60, No. 5, Jan. 2003, pp. 495-506.
Ward et al., Omega-3/6 Fatty Acids: Alternative Sources of Production, Process Biochemistry, vol. 40, No. 12, Dec. 2005, pp. 3627-3652.
Wong, Flavourzyme: A Purified Enzyme Mixture from A. Oryzae, Available Online at: https://controlledmold.com/flavourzyme-a-purified-enzyme-mixture-from-a-oryzae/, Jun. 4, 2021, 8 pages.
Wu et al., Effect of Culture Conditions on Docosahexaenoic Acid Production by Schizochytrium Sp. S31, Process Biochemistry, vol. 40, No. 9, Sep. 2005, pp. 3103-3108.
Yaguchi et al., Production of High Yields of Docosahexaenoic Acid by Schizochytrium sp. Strain SR21, Journal of the American Oil Chemists' Society, vol. 74, No. 11, Nov. 1997, pp. 1431-1434.
Yokochi et al., Optimization of Docosahexaenoic Acid Productions by Schizochytrium Limacinum SR21, Applied Microbiology and Biotechnology, vol. 49, No. 1, Jan. 1998, pp. 72-76.
Zhu et al., Changes of Lipid Content and Fatty Acid Composition of Schizochytrium Limacinum in Response to Different Temperatures and Salinities, Process Biochemistry, vol. 42, No. 2, Feb. 2007, pp. 210-214.
CL202202700, "Office Action", Jul. 31, 2024, 23 pages.
CN202180034488.8 , "Office Action", Jul. 11, 2024, 10 pages.
EP21780736.1 , "Partial Supplementary European Search Report", Jun. 10, 2024, 14 pages.
AEP6002051/2022, "Office Action", Oct. 10, 2024, 10 pages.
CA3172997, "Office Action", Sep. 20, 2024, 6 pages.
PH-1-2022-552593, "Substantive Examination Report", Dec. 9, 2024, 6 pages.
Application No. JP2022-559961, Office Action, Mailed On Jan. 28, 2025, 8 pages.
"Alcalase 2.4 L FG Data Sheet", Strem Chemicals, Inc., Claim No. HP-2023-00001, May 7, 2024, 6 pages.
"Alcalase 2.4 L FG Product Data Sheet", Univar Solutions, Claim No. HP-2023-00001, Exhibit DJK-9, May 7, 2024, 3 pages.
"Alcalase 2.4 L Food Grade Product Sheet", Novozymes A/S, Jul. 3, 2024, 5 pages.
"Alcalase Enzyme Bacillus licheniformis", Merck KGaA, Claim No. HP-2023-000001, May 7, 2024 8 pages.
"Corolase APC Product Data Sheet", AB Enzymes, Claim No. HP-2023-00001, May 7, 2024, 3 pages.
"Fourth Expert Report of Dr. David John Kyle", Claim No. HP-2023-000001, Oct. 8, 2024, 4 pages.
"FSAI Opinion", Particulars of Infringement, Claim No. HP-2023-000001, May 7, 2024, 3 pages.
"Mara Certificate of Analysis of 20205521LG", Particulars of Infringement, Claim No. HP-2023-00001, May 7, 2024, 2 pages.
"Mara Certificate of Analysis of 20227321LG", Particulars of Infringement, Claim No. HP-2023-00001, May 7, 2024, 2 pages.
"Mara fatty acid profile range", Particulars of Infringement, Claim No. HP-2023-000001, May 7, 2024, 2 pages.
"Mara regulatory approval bundle", Particulars of Infringement, Claim No. HP2023-000001, May 7, 2024, 133 pages.
"Protease from Bacillus licheniformis Product Page", Merk KGaA, Claim No. HP-2023-00001, May 7, 2024 10 pages.
"Redacted First Expert Report of Daniel Gary Dueppen", Claim No. HP-2023-000001, Exhibits DGD1 through DGD7, Jul. 3, 2024, 77 pages.
"Redacted First Expert Report of David J. Kyle", Claim No. HP-2023-000001, Exhibits DJK1 to DJK16, Jul. 3, 2024, 147 pages.
"Redacted Second Expert Report of Daniel Gary Dueppen", Claim No. HP-2023-000001, Exhibits DGD8 to DGD12, Aug. 21, 2024, 42 pages.
"Redacted Second Expert Report of David J. Kyle", HP-2023-000001, Exhibits DJK17 to DJK20, Aug. 21, 2024, 19 pages.
"Regulatory Approval Summary Bundle", Claim No. HP-2023-00001, Exhibit DGD-12, Aug. 21, 2024, 62 pages.
"Third Expert Report of Dr. David John Kyle", Claim No. HP-2023-00001, Sep. 19, 2024, 12 pages.
"US & UK Regulatory Filings Summary", Claim No. HP-2023-00001, Exhibit DGD11, Aug. 21, 2024, 3 pages.
Andrews et al., "Enzymatic lysis and disruption of microbial cells", Trends in Biotechnology 5.10 (1987), 6 pages.
Chamberlain et al., "Cytochemical and Ultrastructural Studies on the Cell Walls of Thraustochytrium supp.", Botanica Marina 23.11, Exhibit DJK-26, 1980, 10 pages.
Cohen et al., "Single cell oils", Chapter 6, Exhibit DGD-2, 2005, 11 pages.
Cohen , "Single cell oils", Chapter 3, Exhibit DGD-3, 2005, 13 pages.
Cohen et al., "Single cell oils", Chapter 5, 2005, 16 pages.
Cohen et al., "Single cell oils", Chapter 1, 2005, 23 pages.
Cohen et al., "Single cell oils.", Chapter 13, 2005, 22 pages.
EP2576801 , "Comments from the Comptroller", Claim No. HP-2023-000001, Jun. 25, 2024, 2 pages.
EP3530740 , "Comments from the Comptroller", Claim No. HP-2023-000001, Jun. 25, 2024, 3 pages.
Gruenwald , "Global Nutritional", Nutraceuticals Now, May 15, 2018, 5 pages.
Honda et al., "Molecular phylogeny of labyrinthulids and thraustochytrids based on the sequencing of 18S ribosomal RNA gene", Journal of Eukaryotic Microbiology 46.6, 1999, 12 pages.
HP-2023-000001, "Amended Statement of Reasons for Amendment of EP(UK) 3530740B1", May 7, 2024, 8 pages.
HP-2023-000001, "Defendants' Amended Statement of Opposition to First Claimant's Application to Amend EP(UK) 3530740B1", May 9, 2024, 4 pages.
HP-2023-000001 , "Defendants' Statement of Opposition to First Claimant's Application to Amend EP(UK) 2576801 B1", Jul. 2, 2024, 2 pages.
HP-2023-000001, "Statement of Reasons for Amendment of EP(UK) 2576801B1", Dec. 13, 2023, 4 pages.
HP-2023-000001, "Table 2 : Typical Fatty Acid Composition of Various Commercially Available Fish Oils", Exhibit JPW-2, Jul. 3, 2024, 2 pages.
Kyle et al., "Industrial applications of single cell oils", Chapter 16, AOCS Publishing, 1992, 17 pages.
Moss, "The biology of marine fungi", CUP Archive, Exhibit DJK-27, 1986, 10 pages.
Raghukumar, "Ecology of the marine protists, the Labyrinthulomycetes (Thraustochytrids and Labyrinthulids)", European journal of protistology 38.2, Exhibit JPW-7, 2002, 20 pages.
Ratledge et al., "The biochemistry and molecular biology of lipid accumulation in oleaginous microorganisms", Advances in applied microbiology 51, Exhibit JPW-3, 2002, 53 pages.
Ratledge, "Microorganisms as Sources of Polyunsaturated Fatty Acids", Structured and Modified Lipds, edited by Frank D. Gunnstone, CRC Press, 2001, 53 pages.
Schutte et al., "Pilot- and Process-Scale Techniques for Cell Disruption", Biotechnology and Applied Biochemistry. vol. 12 (1990), 23 pages.
Shahidi et al., "Omega-3 fatty acids: chemistry, nutrition, and health effects.", American Chemical Society, Exhibit DJK-25, 2001, 21 pages.

(56) References Cited

OTHER PUBLICATIONS

Signh et al., "Production of high yields of docosahexaenoic acid by Thraustochytrium roseum ATCC 28210", Journal of industrial microbiology and biotechnology 16.6 (1996), 370-373.

Tjahjono et al., "Formation and regeneration of protoplast from a unicellular green alga *Haematococcus pluvialis*", Journal of fermentation and bioengineering 75.3 (1993), 6 pages.

Cheng et al., "A New Strategy for Strain Improvement of *Aurantiochytrium* Sp. Based on Heavy-ions Mutagenesis and Synergistic Effects of Cold Stress and Inhibitors of Enoyl-ACP Reductase", Enzyme and Microbial Technology vol. 93, Aug. 30, 2016, pp. 182-190.

CL202202700, "Office Action", Feb. 17, 2025, 22 pages.

EP21780736.1, "Extended European Search Report", Mar. 3, 2025, 20 pages.

\* cited by examiner

MICROBIAL OILS WITH HIGH LEVELS OF OMEGA-3 FATTY ACIDS

CROSS-REFERENCE TO RELATED APPLICATIONS

This application claims priority to U.S. Provisional Application No. 63/005,054, filed Apr. 3, 2020, which is incorporated by reference herein in its entirety.

BACKGROUND

Oil from microorganisms is produced as a result of two parallel fatty acid synthesis pathways: the classical fatty acid synthesis (FAS) pathway and the polyunsaturated fatty acid (PUFA) synthase pathway. Medium chain fatty acids like myristic (C14:0) and palmitic acid (C16:0) are generally produced from the FAS pathway and long chain polyunsaturated fatty acids (LC-PUFA) like docosahexaenoic acid (DHA, C22:6 n-3) and docosapentaenoic acid (DPA, C22:5 n-6) are generally produced from the PUFA synthase pathway. The resultant fatty acid profile, however, varies greatly across microorganisms, depending on the relative activity of these parallel pathways.

BRIEF SUMMARY

Provided herein are microbial oils and methods of making and using microbial oils with high levels of omega-3 fatty acids. Specifically, provided is a microbial oil comprising at least 85% total fatty acids by weight, wherein the total fatty acids comprise at least 50% DHA by weight. Also provided is a method of making a biomass comprising culturing an oil-producing microorganism (e.g., Aurantiochytrium) in a culture medium comprising a fatty acid synthesis inhibitor, wherein the biomass comprises at least 500 mg/g oil.

DETAILED DESCRIPTION

Omega-3 fatty acids, including docosahexaenoic acid (DHA, C22:6 n-3) and eicosapentaenoic acid (EPA, C20:5 n-3) from the long chain-polyunsaturated fatty acid (LC-PUFA) family, are essential fatty acids for humans and non-human mammals. The amount of omega-3 fatty acids required in a microbial oil varies based on applications. For example, dietary supplements and pharmaceuticals typically prefer higher concentrations of omega-3 fatty acids per unit of oil. To achieve such concentrations, the omega-3 fatty acids are typically concentrated by transesterification and molecular distillation (Bonilla-Mendez and Hoyos-Concha, *Corpoica Cienc Tecnol Agropecuaria, Mosquera* (Colombia), 19 (3): 645-668 (2018)). However, the final concentrated products are typically in ethyl-ester (EE) chemical form instead of the triglyceride (TG) form, the natural chemical structure when the lipids are synthesized by microorganisms. Not only does the EE form require additional processing that may compromise its olfactory characteristics, it has also been shown that the EE form of omega-3 is less bioavailable to the human body than the original TG form.

Common strategies to increase omega-3 content include selecting high omega-3 microbial strains, classical mutagenesis, and genetic modification (Lian et al., Appl Biochem Biotechnol, 162:935-941 (2010)). Alternatively, chemicals with potential to affect the fatty acid synthesis metabolism under various mechanisms have been tested in different microorganisms. However, efficient and effective methods of applying such principles to achieve a commercially meaningful increase in DHA content while avoiding or minimizing any undesirable changes in other fatty acid components, including DPA and saturated fatty acids, are lacking.

Described herein are oils containing high levels of omega-3 fatty acid with DHA accounting for approximately 50-70% of the fatty acid profile. Also described are methods using fatty acid synthesis inhibitors to suppress less-desirable products of the FAS pathway in favor of the high-value PUFA products from the PUFA synthase pathway. The provided oils contain high concentrations of DHA without sacrificing the productivity of the microorganism. Further, described are methods of using inhibitors that inhibit the fatty acid synthase multienzyme complex as described herein. The examples illustrate fatty acid profiles of G3, showing a substantial increase in DHA content (up to more than 83.3% when compared to the control) and even more with pulsed-addition of a fatty acid synthesis inhibitor. The outcome of almost 70% DHA in TG form in an oil exceeds reported DHA concentrations.

Microorganisms, including Thraustochytrids, produce oil containing a variety of lipids, including fatty acids in various forms and amounts. As used herein, the term lipid includes phospholipids, free fatty acids, esters of fatty acids, triacylglycerols, sterols and sterol esters, carotenoids, xanthophylls (e.g., oxycarotenoids), hydrocarbons, and other lipids known to one of ordinary skill in the art. Fatty acids are hydrocarbon chains that terminate in a carboxyl group, being termed unsaturated if they contain at least one carbon-carbon double bond, and polyunsaturated when they contain multiple carbon-carbon double bonds. For example, microorganisms can produce (i) short-chain fatty acids (SCFA), which are fatty acids with aliphatic tails of fewer than six carbons (e.g., butyric acid); (ii) medium-chain fatty acids (MCFA), which are fatty acids with aliphatic tails of 6-12 carbons; (iii) long-chain fatty acids (LCFA), which are fatty acids with aliphatic tails of greater than 13 carbons. Various microorganisms produce varying types and amounts of these fatty acids. Provided herein are microorganisms and methods that shift production of these fatty acids away from medium-chain fatty acids produced by the FAS pathway to long-chain fatty acids produced by the PUFA synthase pathway. Fatty acid synthesis (FAS) is defined as the creation of fatty acids from acetyl-CoA and NADPH through the action of enzymes called fatty acid synthases. The PUFA synthase pathway enables the synthesis of polyunsaturated fatty acids de novo from malonyl-CoA by large multidomain, multi-subunit enzymes. The major end-product of the FAS pathway is palmitate, while the major end-product of the PUFA synthases are PUFAs such as DHA and DPA.

Thus, provided herein are microbial oils and methods for making and using microbial oils. The oils include fatty acids in the form of monoglycerides, diglycerides, and triglycerides, as well as free fatty acids and phospholipids. Optionally, the microbial oil comprises at least 90% (e.g., 91%, 92%, 93%, 94%, 95%, 96%, 97%, 98%, or 99%) triglycerides. Optionally, the microbial oil comprises at least 95% triglycerides.

The oils also contain at least 85% (e.g., 86%, 87%, 88%, 89%, 90%, 91%, 92%, 93%, 94%, 95%, 96%, 97%, 98%, or 99%) by weight total fatty acids (TFA). Optionally, the oil contains between 85% to 99% total fatty acids by weight. Optionally, the microbial oil comprises 85% to 95% total fatty acids by weight. Optionally, the microbial oil comprises at least 90% total fatty acids by weight.

The percentages in reference to oils or total fatty acids are recited throughout by weight percent. For example, when a microbial oil comprises at least 90% total fatty acids, the oil contains at least 90% total fatty acids by weight of the oil. Also, total fatty acids contain specific fatty acids and percentages of the specific fatty acid are expressed throughout as weight % of the total fatty acids. For example, when the total fatty acids in the oil contain DHA, the amount of DHA is expressed as weight % of the total fatty acids. For example, the total fatty acids comprise at least 50% DHA by weight.

As described, the total fatty acids of the provided oils contain DHA. Optionally, the total fatty acids comprise at least 35%, at least 40%, or at least 45% DHA. Optionally, the total fatty acids comprise at least 50% DHA. Optionally, the total fatty acids include at least 60% DHA. Optionally, the total fatty acids include 50% to 70% DHA. Optionally, the total fatty acids comprise 60% to 70% DHA.

Optionally, the oil also contains between 6% to 18% DPA. Optionally, the oil contains between 10% to 18% DPA. Optionally, the oil contains between 6% to 10% DPA. Optionally, the total fatty acids comprise at least 60% DHA and between 10% by weight to 18% DPA. Optionally, the ratio of DHA to DPA is less than or equal to 7:1 or 6:1. Optionally, the total fatty acids comprise at least 50% DHA and the ratio of DHA to DPA is less than or equal to 7:1. Optionally, the total fatty acids comprise at least 50% DHA and the ratio of DHA to DPA is less than or equal to 6:1.

Optionally, the oil contains less than 1% stearic acid. Optionally, the total fatty acids comprise 0.01% to 1% stearic acid or 0.001% to 1% by weight stearic acid.

Optionally, the microbial oil comprises at least 85% total fatty acids, wherein the total fatty acids comprise at least 50% DHA, between 6% to 18% DPA, and less than 1% stearic acid. Optionally, the microbial oil comprises at least 85% total fatty acids, wherein the total fatty acids comprise at least 60% DHA.

Optionally, the total fatty acids comprise less than 3%, 2% or 1% eicosapentaenoic acid. Optionally, the total fatty acids comprise 0.01% to 1% eicosapentaenoic acid or 0.001% to 1% eicosapentaenoic acid. Optionally, the total fatty acids comprise 0.01% to 2% eicosapentaenoic acid or 0.001% to 2% eicosapentaenoic acid. Optionally, the total fatty acids comprise 0.01% to 3% eicosapentaenoic acid or 0.001% to 3% eicosapentaenoic acid.

Optionally, the total fatty acids comprise less than 5%, less than 4%, or less than 3% pentadecanoic acid. Optionally, the total fatty acids comprise 0.01% to 3%, 0.01% to 4%, or 0.01% to 5% pentadecanoic acid.

Optionally, the total fatty acids comprise less than 45%, 40%, 35%, 30%, or 25% saturated fatty acids (SFAs). Saturated fatty acids in the oils produced by the herein described method include, but are not limited to, C12:0 (lauric acid), C14:0 (myristic acid), C15:0 (pentadecanoic acid), C16:0 (palmitic acid), C17:0 (heptadecanoic acid), and C18:0 (stearic acid). Optionally, the total fatty acids comprise between 10% and 45% saturated fatty acids (e.g., 10% and 40%, 10% and 30, 10% and 20%, 15% and 30%, 15% and 20%, 20% and 30%, or 20% and 25% saturated fatty acids).

Optionally, the total fatty acids comprise 0.001% to 2.0% (e.g., 0.01% to 2.0% or 0.05% to 2.0%) arachidonic acid (C20:4 (n-6)). Optionally, the total fatty acids comprise 0.001% to 1% (e.g., 0.01% to 1%) eicosatetraenoic acid (C20:4 (n-3)).

Optionally, the total fatty acids comprise less than 5% by weight myristic acid. Optionally, the total fatty acids comprise 0.001% to 5%, (e.g., 0.01% to 5%, 0.1% to 5%, 0.01% to 4%, 0.1% to 4% or 1% to 4%) by weight myristic acid.

Optionally, the total fatty acids comprise less than 40% by weight palmitic acid. Optionally, the total fatty acids comprise between 5% and 40%, 5% and 30%, 10% and 40%, 10% and 30%, 20% and 40%, 20% and 30%, 20% and 40%, 20% and 25%, or 25% and 40% by weight palmitic acid.

Optionally, the total fatty acids comprise 0.1% to 0.5% or 0.001% to 0.5% by weight heptadecanoic acid.

Optionally, the fatty acids in the biomass or isolated therefrom comprise less than 3% by weight eicosapentaenoic acid, less than 5% by weight pentadecanoic acid, and less than 45% saturated fatty acids.

Optionally, the fatty acids in the biomass or isolated therefrom comprise 0.001% to 2.0%, 0.01% to 2.0%, or 0.05% to 2.0% arachidonic acid, less than 5% by weight myristic acid, and less than 40% by weight palmitic acid.

Also provided are microbial biomasses comprising oil. The microbial biomass comprises between 40 to 75% total fatty acids by weight of the total biomass. Optionally, the oil in the biomass comprises DHA and the biomass comprises 20% to 55% DHA by weight of the biomass. Optionally, the oil in the biomass comprises between 2.5% to 8% DPA by weight of the biomass. Optionally, the oil contains between 4% to 8% DPA by weight of the biomass. Optionally, the oil contains between DPA 2.5% to 4% by weight of the biomass.

Eukaryotic microorganisms useful for producing the provided microbial oils and biomasses include, but are not limited to, microorganisms selected from the genus Oblongichytrium, Aurantiochytrium, Thraustochytrium, Schizochytrium, and *Ulkenia* or any mixture thereof. Optionally, the oil-producing eukaryotic microorganisms are microorganisms with an 18S sequence with at least 97%, 98%, 99% or 100% identity to the nucleic acid sequence set forth in SEQ ID NO:1. Optionally, the oil-producing microorganisms are microorganisms of the strain Aurantiochytrium limacinum. Optionally, the eukaryotic microorganism is the same as the microorganism deposited with the International Depositary Authority of Canada (IDAC), National Microbiology Laboratory, Public Health Agency of Canada, 1015 Arlington Street, Winnipeg, Manitoba Canada R3E 3R2, on Jul. 22, 2016, having IDAC assigned Accession No. 220716-01. This deposit will be maintained under the terms of the Budapest Treaty on the International Recognition of the Deposit of Microorganisms for the Purposes of Patent Procedure. This deposit is exemplary and was made merely as a convenience for those of skill in the art and is not an admission that a deposit is required for patentability. The terms "G3," "G3-1" or "G3-1 strain" or "strain G3-1" are used herein interchangeably to refer to the eukaryotic microorganism having IDAC Accession No. 220716-01.

Nucleic acid, as used herein, refers to deoxyribonucleotides or ribonucleotides and polymers and complements thereof. The term includes deoxyribonucleotides or ribonucleotides in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, and peptide-nucleic acids (PNAs). Unless otherwise indicated, conservatively modified variants of nucleic acid sequences (e.g., degenerate codon substitutions) and complementary sequences can be used in place of a particular nucleic acid sequence recited herein. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); Rossolini et al., Mol. Cell. Probes 8:91-98 (1994)). The term nucleic acid is used interchangeably with gene, cDNA, RNA, oligonucleotide, and polynucleotide.

The terms identical or percent identity, in the context of two or more nucleic acids or polypeptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site or the like). Such sequences are then said to be substantially identical. This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

For sequence comparison, typically one sequence acts as a reference sequence to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated as appropriate. The sequence comparison algorithm then calculates the percent sequence identities for the test sequences relative to the reference sequence based on the program parameters.

A comparison window, as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, Adv. Appl. Math. 2:482 (1981); by the homology alignment algorithm of Needleman & Wunsch, J. Mol. Biol. 48:443 (1970); by the search for similarity method of Pearson & Lipman, Proc. Nat'l. Acad. Sci. USA 85:2444 (1988); by computerized implementations of these algorithms (GAP, BESTFIT, FASTA, and TFASTA in the Wisconsin Genetics Software Package, Genetics Computer Group, 575 Science Dr., Madison, WI); or by manual alignment and visual inspection (see, e.g., Current Protocols in Molecular Biology (Ausubel et al., eds. 1995 supplement)).

A preferred example of an algorithm that is suitable for determining percent sequence identity and sequence similarity are the BLAST and BLAST 2.0 algorithms, which are described in Altschul et al., Nuc. Acids Res. 25:3389-3402 (1977), and Altschul et al., J. Mol. Biol. 215:403-410 (1990), respectively. BLAST and BLAST 2.0 are used, with the parameters described herein, to determine percent sequence identity for nucleic acids or proteins. Software for performing BLAST analyses is publicly available through the National Center for Biotechnology Information, as known in the art. This algorithm involves first identifying high scoring sequence pairs (HSPs) by identifying short words of a selected length (W) in the query sequence, which either match or satisfy some positive-valued threshold score T when aligned with a word of the same length in a database sequence. T is referred to as the neighborhood word score threshold (Altschul et al.). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The Expectation value (E) represents the number of different alignments with scores equivalent to or better than what is expected to occur in a database search by chance. The BLASTN program (for nucleotide sequences) uses as defaults a wordlength (W) of 11, an expectation (E) of 10, M=5, N=-4 and a comparison of both strands. For amino acid sequences, the BLASTP program uses as defaults a wordlength of 3, expectation (E) of 10, and the BLOSUM62 scoring matrix (see Henikoff & Henikoff, Proc. Natl. Acad. Sci. USA 89:10915 (1989)), alignments (B) of 50, expectation (E) of 10, M=5, N=-4, and a comparison of both strands.

Provided herein are methods of making biomass using oil-producing microorganisms. Specifically, provided is a method of making a biomass comprising culturing an oil-producing Aurantiochytrium microorganism in a culture medium comprising a fatty acid synthesis inhibitor, wherein the biomass comprises at least 350, 400, 450 or 500 mg/g oil. The biomass can be used for making an oil having the characteristics described herein. The method further comprises isolating the oil from the biomass.

The culturing step can be carried out at a temperature of 15° C. to 28° C. (e.g., 15, 16, 17, 18, 19, 20, 21, 22, 23, 24, 25, 26, 27 or 28° C.). Optionally, the culture medium is at a temperature of 18° C. to 22° C., 22° C. to 28° C., 22° C. to 25° C., or 25° C. to 28° C.

The fatty acid synthesis inhibitor can be added to the culture medium before, after or concurrently with addition of the microorganisms to the culture medium. Optionally, the fatty acid synthesis inhibitor is fed to the culture medium either continuously or intermittently. Optionally, the method further comprises adding the microorganisms to the culture medium and then adding the fatty acid synthesis inhibitor to the culture medium at least 6, 12, 24 or 48 hours after addition of the microorganisms to the culture medium. Optionally, the method further comprises adding the microorganisms to the culture medium and then adding the fatty acid synthesis inhibitor to the culture medium between 24 to 48 hours after addition of the microorganisms to the culture medium. Optionally, the method further comprises adding the microorganisms to the culture medium and then adding the fatty acid synthesis inhibitor to the culture medium between 6 to 24 hours after addition of the microorganisms to the culture medium. Optionally, the method further comprises adding the microorganisms to the culture medium and then adding the fatty acid synthesis inhibitor to the culture medium between 12 to 24 hours after addition of the microorganisms to the culture medium.

The fatty acid synthesis inhibitor can be added to the culture medium in one or more doses. Optionally, the method further comprises adding the microorganisms to the culture medium and the culturing comprises adding the fatty acid synthesis inhibitor in 1, 2, 3, 4, 5, or 6 doses, for example, beginning 6, 12, 24, or 48 hours after addition of the microorganisms to the culture medium. Optionally, the one or more doses are added every 6, 12, or 24 hours. By way of example, 3 doses of the fatty acid inhibitor can be added to the culture medium every 12 hours starting 24 hours after the microorganisms are added to the culture medium.

The total amount of fatty acid synthesis inhibitor added to the culture medium comprises between 3 μM and 40 μM. Optionally, the fatty acid synthesis inhibitor is administered in one or multiple doses (e.g., 2, 3, 4, 5, 6, 7, 8, 9, or 10 doses) amounting to a total of inhibitor between 3 μM and 40 μM. For example, the fatty acid synthesis inhibitor can be added in 6 doses of 2 μM amounting to a total of 12 μM. By way of other examples, the fatty acid synthesis inhibitor can be added 3 times at doses of 1, 2, 3, or 8 μM. Optionally, the fatty acid synthesis inhibitor can be added 6 times at doses of 0.5, 1, 2, 3, and 4 μM. Optionally, the total concentration of the fatty acid synthesis inhibitor added to the culture medium during the culturing comprises between 30 μg and 700 μg of inhibitor per gram of biomass. Optionally, the fatty acid synthesis inhibitor is administered in 1, 2, 3, 4, 5, 6, 7, 8, 9, or 10 doses amounting to between 30 μg and 700 μg per gram of biomass. By way of example, the fatty acid synthesis inhibitor can be added in 6 doses of 40 μg per gram of biomass amounting to a total of 240 μg. By way of other examples, the fatty acid synthesis inhibitor can be added 3 times at doses of approximately 12, 24, 42, and 120 μg per gram of biomass. Optionally, the fatty acid synthesis inhibitor can be added 6 times at doses of 5.5, 11, 25, 40 and 62 μg per gram of biomass.

Suitable fatty acid synthesis inhibitors include, but are not limited to fatty acid synthase inhibitors. Optionally, the fatty acid synthase inhibitor is selected from the group consisting of quercetin, α-mangostin, thiolactomycin, triclosan, isoniazid, decynoyl-N-acetylcysteamine (NAC), and cerulenin.

As described above, eukaryotic microorganisms useful for the provided methods include, but are not limited to, microorganisms selected from the genus Oblongichytrium, Aurantiochytrium, Thraustochytrium, Schizochytrium, and Ulkenia or any mixture thereof. Optionally, the oil-producing eukaryotic microorganisms are microorganisms with an 18S sequence with at least 97%, 98%, 99% or 100% identity to the sequence set forth in SEQ ID NO: 1. Optionally, the eukaryotic microorganism has IDAC Accession No. 220716-01.

As described herein, the biomass comprises fatty acids, e.g., fatty acids comprising at least at least 90%, 91%, 92%, 93%, 94%, 95%, 96%, 97%, 98%, or 99% triglycerides as described above. Oils in the biomass also contain at least 85%, total fatty acids by weight as described above.

Optionally, the fatty acids isolated from the biomass comprise at least 50% DHA by weight as described above.

The fatty acids in the biomass optionally comprise between 6% to 18% DPA by weight as described above. Optionally, the ratio of DHA to DPA in the fatty acids, the oil in the biomass, or isolated therefrom is less than or equal to 7:1 or 6:1 as described above.

The oil in the biomass or isolated therefrom optionally contains less than 1% by weight stearic acid as described above.

Optionally, the fatty acids in the biomass or isolated therefrom comprise less than 3% by weight eicosapentaenoic acid, less than 5% by weight pentadecanoic acid, and less than 45% saturated fatty acids as described above.

Optionally, the fatty acids in the biomass or isolated therefrom comprise 0.001% to 2.0% or 0.01% to 2.0% or 0.05% to 2.0%, arachidonic acid, less than 5% by weight myristic acid, and less than 40% by weight palmitic acid. Optionally, the fatty acids comprise 0.1% to 0.5% or 0.001% to 0.5% by weight heptadecanoic acid.

Culture medium as used in the described methods supplies various nutritional components, including a carbon source and a nitrogen source, for the microorganisms.

Medium for culture can include any of a variety of carbon sources. Examples of carbon sources include fatty acids, lipids, glycerols, triglycerols, carbohydrates, polyols, amino sugars, and any kind of biomass or waste stream. Fatty acids include, for example, oleic acid. Carbohydrates include, but are not limited to, glucose, cellulose, hemicellulose, fructose, dextrose, xylose, lactulose, galactose, maltotriose, maltose, lactose, glycogen, gelatin, starch (corn or wheat), acetate, m-inositol (e.g., derived from corn steep liquor), galacturonic acid (e.g., derived from pectin), L-fucose (e.g., derived from galactose), gentiobiose, glucosamine, alpha-D-glucose-1-phosphate (e.g., derived from glucose), cellobiose, dextrin, alpha-cyclodextrin (e.g., derived from starch), and sucrose (e.g., from molasses). Polyols include, but are not limited to, maltitol, erythritol, and adonitol. Amino sugars include, but are not limited to, N-acetyl-D-galactosamine, N-acetyl-D-glucosamine, and N-acetyl-beta-D-mannosamine. The carbon source can be present in the heterotrophic medium at a concentration of 200 g/L, 175 g/L, 150 g/L, 100 g/L, 60 g/L or less, e.g., at a concentration of 1 to 200 g/L, 5 to 200 g/L, 10 to 200 g/L, 50 to 200 g/L, or 100 to 200 g/L.

The microorganisms can be cultured in medium having a chloride concentration from about 0.5 g/L to about 50.0 g/L (e.g., a chloride concentration from about 0.5 g/L to about 35 g/L, from about 18 g/L to about 35 g/L, or from about 2 g/L to about 35 g/L). The microorganisms described herein can be grown in low chloride conditions, e.g., from about 0.5 g/L to about 20 g/L, or from about 0.5 g/L to about 15 g/L.

The culture medium optionally includes NaCl. The culture medium can include non-chloride-containing sodium salts as a source of sodium. Examples of non-chloride sodium salts suitable for use in accordance with the present methods include, but are not limited to, soda ash (a mixture of sodium carbonate and sodium oxide), sodium carbonate, sodium bicarbonate, sodium sulfate, and mixtures thereof. See, e.g., U.S. Pat. Nos. 5,340,742 and 6,607,900, the entire contents of each of which are incorporated by reference herein. Optionally, the medium comprises 9 g/L chloride when using 20 g/L of carbon, 20 g/L soy peptone, and 5 g/L yeast extract. The medium can comprise 35 g/L chloride when the medium contains 10 g/L carbon, 5 g/L soy peptone, 5 g/L yeast extract and 10 g/L agar. The medium can comprise 2 g/L chloride when the medium contains 20-40 g/L carbon, 1 g/L yeast extract, 1-20 g/L monosodium glutamate (MSG), 0.3-2.0 g/L phosphates, 4 g/L magnesium sulfate, 5-10 g/L ammonium sulfate, 1.5 mL/L trace elements solution, 1 mL/L of vitamin B solution, and 0.1 g/L $CaCl_2$).

Medium for a microorganism culture can include any of a variety of nitrogen sources. Exemplary nitrogen sources include ammonium solutions (e.g., $NH_4$ in $H_2O$), ammonium or amine salts (e.g., $(NH_4)_2SO_4$, $(NH_4)_3PO_4$, $NH_4NO_3$, $NH_4OOCH_2CH_3(NH_4Ac)$), peptone, soy peptone, tryptone, yeast extract, malt extract, fish meal, sodium glutamate, soy extract, casamino acids and distiller grains. Concentrations of nitrogen sources in suitable medium typically range between and including about 1 g/L and about 25 g/L (e.g., about 5 to 20 g/L, about 10 to 15 g/L, or about 20 g/L). Optionally, the concentration of nitrogen is about 10 to 15 g/L when yeast extract is the source of complex nitrogen in the medium. Optionally, the concentration of nitrogen is about 1 to 5 g/L when soy peptone is in the medium along with L-Glutamic acid monosodium salt hydrate (MSG) or ammonium sulfate.

The medium optionally includes a phosphate, such as potassium phosphate or sodium-phosphate (e.g., potassium phosphate monobasic).

Inorganic salts and trace nutrients in the medium can include ammonium sulfate, sodium bicarbonate, sodium orthovanadate, potassium chromate, sodium molybdate, selenous acid, nickel sulfate, copper sulfate, zinc sulfate, cobalt chloride, iron chloride, manganese chloride calcium chloride, and EDTA. Optionally, the medium includes at least 1.5 ml/L of a trace element solution. Optionally, the trace element solution comprises 2 mg/mL copper (II) sulfate pentahydrate, 2 mg/mL zinc sulfate heptahydrate, 1 mg/mL cobalt (II) chloride hexahydrate, 1 mg/mL manganese (II) chloride tetrahydrate, 1 mg/mL sodium molybdate dihydrate, and 1 mg/mL nickel (II) sulfate.

The medium can include magnesium sulfate, optionally, with a trace element solution and/or potassium phosphate monobasic.

Vitamins such as pyridoxine hydrochloride, thiamine hydrochloride, calcium pantothenate, p-aminobenzoic acid, riboflavin, nicotinic acid, biotin, folic acid and vitamin B12 can be included in the culture medium.

The pH of the medium can be adjusted to between and including 3.0 and 10.0 using acid or base, where appropriate, and/or using the nitrogen source. Optionally, the medium is sterilized.

Generally a medium used for culture of a microorganism is a liquid medium. However, the medium used for culture of a microorganism can be a solid medium. In addition to carbon and nitrogen sources as discussed herein, a solid medium can contain one or more components (e.g., agar and/or agarose) that provide structural support and/or allow the medium to be in solid form.

Cultivation of the microorganisms can be carried out using known conditions, for example, those described in International Publication Nos. WO 2007/069078 and WO 2008/129358. For example, cultivation can be carried out for 1 to 30 days (e.g., 1 to 21 days, 1 to 15 days, 1 to 12 days, 1 to 9 days, or 3 to 5 days). Cultivation can be carried out at temperatures between 4 to 30° C. Optionally, cultivation is carried out by aeration-shaking culture, shaking culture, stationary culture, batch culture, fed-batch culture, continuous culture, rolling batch culture, wave culture, or the like. Optionally, cultivation is carried out with a dissolved oxygen content of the culture medium between 1 and 20%, between 1 and 10%, or between 1 and 5%.

The biomass as described herein can be incorporated into a final product (e.g., food or feed supplement, biofuel, etc.). Thus, provided is a method of using the protein-rich biomass. The method optionally includes incorporating the protein-rich biomass into a foodstuff (e.g., a pet food, a livestock feed, or an aquaculture feed).

Oils or lipids can be isolated from the described microorganism culture and used in various food and feed supplements. Suitable food or feed supplements into which the oils can be incorporated include beverages such as milk, water, sports drinks, energy drinks, teas, and juices; confections such as candies, jellies, and biscuits; fat-containing foods and beverages such as dairy products; processed food products such as soft rice (or porridge); infant formulae; breakfast cereals; or the like. Optionally, one or more produced lipids can be incorporated into a dietary supplement, such as, for example, a vitamin or multivitamin. Optionally, an oil produced according to the method described herein can be included in a dietary supplement and optionally can be directly incorporated into a component of food or feed (e.g., a food supplement).

Examples of feedstuffs into which oils or lipids produced by the methods described herein can be incorporated include pet foods such as cat foods; dog foods; feeds for aquarium fish, cultured fish or crustaceans, etc.; or feed for farm-raised animals (including livestock and fish or crustaceans raised in aquaculture). Food or feed material into which the oils or lipids produced according to the methods described herein can be incorporated is preferably palatable to the organism which is the intended recipient. This food or feed material can have any physical properties currently known for a food material (e.g., solid, liquid, soft).

Optionally, one or more of the produced compounds (e.g., PUFAs) can be incorporated into a nutraceutical or pharmaceutical product. Examples of such a nutraceutical or pharmaceutical forms include various types of tablets, capsules, drinkable agents, etc. Optionally, the nutraceutical or pharmaceutical is suitable for topical application (e.g., lotion form). Dosage forms can include, for example, capsules, oils, tablets or the like.

The oil or lipids produced according to the methods described herein can be incorporated into products in combination with any of a variety of other agents. For instance, such compounds can be combined with one or more binders or fillers, chelating agents, pigments, salts, surfactants, moisturizers, viscosity modifiers, thickeners, emollients, fragrances, preservatives, etc., or any combination thereof.

Disclosed are materials, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutations of these compounds may not be explicitly disclosed, each is specifically contemplated and described herein. For example, if a method is disclosed and discussed and a number of modifications that can be made to a number of molecules including the method are discussed, each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

Publications cited herein and the material for which they are cited are hereby specifically incorporated by reference in their entireties.

The examples below are intended to further illustrate certain aspects of the methods and compositions described herein, and are not intended to limit the scope of the claims.

EXAMPLES

Example 1. Fatty Acid Synthesis Inhibitor Dose Timing Strategy

Figure 1:
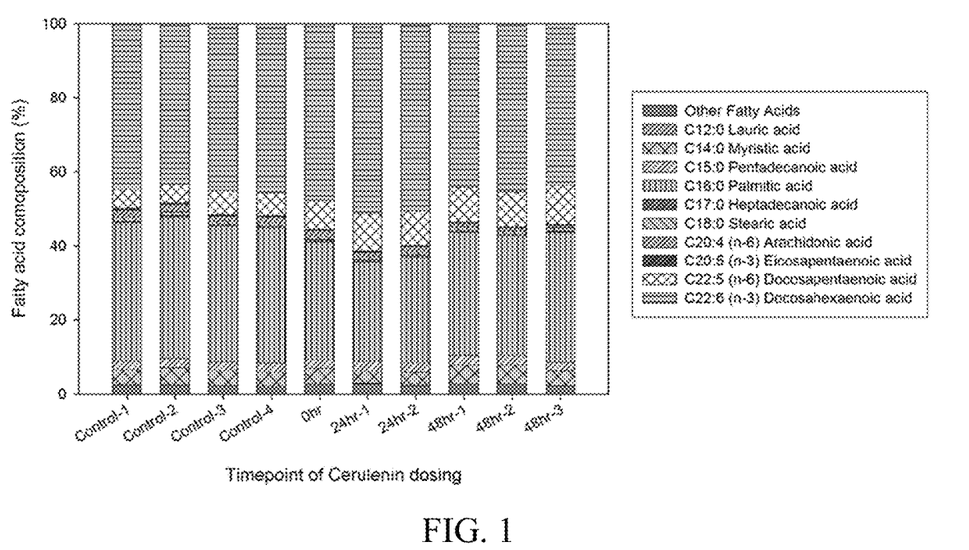
FIG. 1 is a graph showing fatty acid profiles of Aurantiochytrium sp. (G3) utilizing different initial fatty acid synthesis inhibitor dosing timepoints at 20° C.

To determine the ideal time for addition of the fatty acid synthase inhibitor cerulenin without excessive harm such as preventing cell growth, experiments were conducted by adding a set amount of cerulenin at various amounts of time after inoculation. In all experiments, the control experiment was performed with the same medium and growth conditions without the addition of FAS inhibitors. The results demonstrated that cell growth was not inhibited at any addition time, however it did have a significant impact on the fatty acid profile (FIG. 1). Table 2 shows that adding cerulenin 24 hours after inoculation resulted in higher DHA and DPA content (% of TFA) with fatty acid synthesis pathway products C14:0 and C16:0 reduced by 21.1% and 27.9% respectively.

TABLE 1

Fatty acid content (in mg/g) of predominant fatty acids in *Aurantiochytrium* sp. (G3) at 20° C. (except 48 hr). Addition times represent the time of addition of 25 µM cerulenin after inoculation.

Fatty Acid Content (mg/g of dry biomass)

| Time of addition | C14:0 | C16:0 | C17:0 | C20:5 (n-3) | C22:5 (n-6) | C22:6 (n-3) | SFA | TFA | DHA:DPA |
|---|---|---|---|---|---|---|---|---|---|
| Control | 25.50 | 230.24 | 3.07 | 3.10 | 35.26 | 277.28 | 280.75 | 619.90 | 7.98 |
| 0 hr | 23.45 | 183.73 | 4.07 | 1.97 | 45.07 | 276.37 | 232.31 | 579.14 | 6.13 |
| 24 hr | 18.23 | 150.17 | 4.36 | 1.90 | 55.95 | 287.63 | 204.48 | 560.24 | 5.14 |
| 48 hr* | 29.55 | 216.10 | 2.79 | 1.97 | 62.60 | 284.99 | 272.20 | 641.86 | 4.58 |

*From 25° C. data

TABLE 2

Fatty acid content (relative to total fatty acids) of predominant fatty acids in *Aurantiochytrium* sp. (G3) at 20 °C. (except 48 hr). Addition times represent the time of addition of 25 µM cerulenin after inoculation Fatty Acid Content (% of TFA)

| Time of addition | C14:0 | C16:0 | C17:0 | C20:5 (n-3) | C22:5 (n-6) | C22:6 (n-3) | SFA |
|---|---|---|---|---|---|---|---|
| Control | 4.12 | 37.16 | 0.50 | 0.50 | 5.67 | 44.71 | 45.32 |
| 0 hr | 4.05 | 31.73 | 0.70 | 0.34 | 7.78 | 47.72 | 40.11 |
| 24 hr | 3.25 | 26.80 | 0.76 | 0.33 | 9.99 | 51.34 | 35.35 |
| 48 hr* | 4.62 | 33.62 | 0.44 | 0.31 | 9.73 | 44.42 | 42.39 |

*From 25° C. data

Example 2. Fatty Acid Synthesis Inhibitor Concentration

Figure 2:
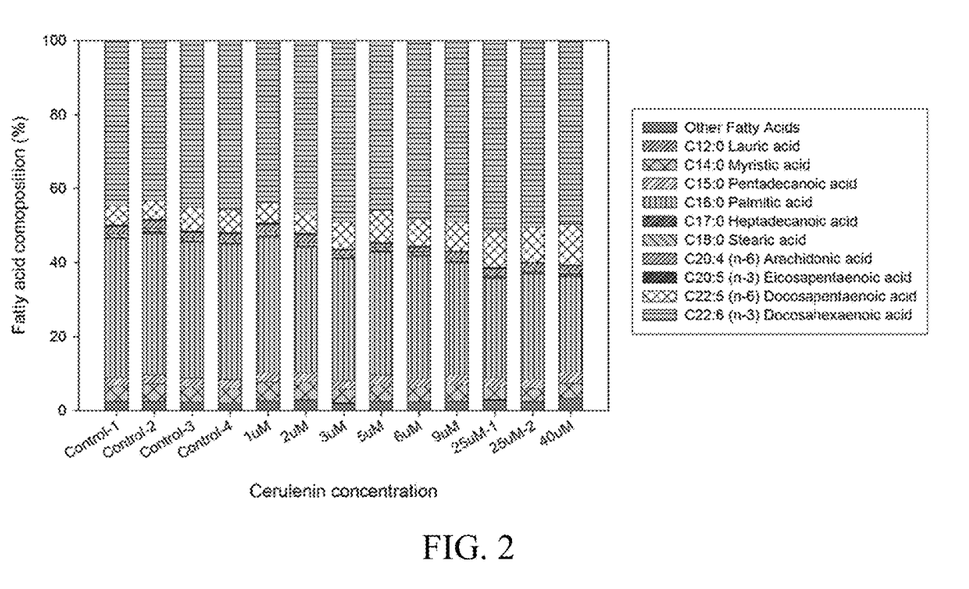
FIG. 2 is a graph showing fatty acid profiles of Aurantiochytrium sp. (G3) in varying concentrations of fatty acid synthesis inhibitor at 20° C.

To determine the optimum concentration of cerulenin to provide the best results, a range of concentrations from 1 µM to 40 µM were tested. For consistency, all cerulenin additions were made at 24 hours after inoculation. FIG. 2 shows the fatty acid profiles of *Aurantiochytrium* sp. (G3) in varying concentrations of cerulenin at 20° C. Table 5 shows that increasing cerulenin concentration has a clear impact on the amount of C16:0 and DPA accumulated in the cells. In terms of percentage of the total fatty acids, those changes in specific fatty acids correspond to an increase in DHA content (% of TFA) from 44.71% to as high as 50.92% when 25 µM of cerulenin is used (Table 4).

TABLE 3

Fatty acid content (mg/g) of predominant fatty acids in *Aurantiochytrium* sp. (G3) at 20° C. with cerulenin added at 24 hours after inoculation.
Fatty Acid Content (mg/g of dry biomass)

| Cerulenin | C14:0 | C16:0 | C17:0 | C20:5 (n-3) | C22:5 (n-6) | C22:6 (n-3) | SFA | TFA | DHA:DPA |
|---|---|---|---|---|---|---|---|---|---|
| Control | 25.50 | 230.24 | 2.93 | 2.69 | 35.26 | 277.28 | 280.75 | 619.90 | 7.98 |
| 1 μM | 28.38 | 211.50 | 3.26 | 3.60 | 29.32 | 256.10 | 265.63 | 580.28 | 8.73 |
| 2 μM | 26.95 | 196.70 | 3.15 | 3.58 | 31.82 | 270.39 | 248.72 | 580.90 | 8.50 |
| 3 μM | 24.49 | 216.49 | 2.95 | 2.15 | 47.79 | 323.48 | 265.09 | 658.72 | 6.77 |
| 6 μM | 24.72 | 204.08 | 3.22 | 2.74 | 43.70 | 300.35 | 252.79 | 619.88 | 6.87 |
| 9 μM | 25.94 | 181.97 | 3.48 | 2.49 | 47.27 | 296.00 | 233.91 | 603.79 | 6.26 |
| 25 μM | 19.16 | 160.27 | 4.36 | 1.90 | 55.84 | 294.31 | 204.48 | 578.10 | 5.27 |
| 40 μM | 21.71 | 138.29 | 4.94 | 1.87 | 59.05 | 268.00 | 188.40 | 540.11 | 4.54 |

TABLE 4

Fatty acid content (relative to total fatty acids) of predominant fatty acids in *Aurantiochytrium* sp. (G3) at 20° C. with cerulenin added at 24 hours after inoculation.
Fatty Acid Content (% of TFA)

| Cerulenin | C14:0 | C16:0 | C17:0 | C20:5 (n-3) | C22:5 (n-6) | C22:6 (n-3) | SFA |
|---|---|---|---|---|---|---|---|
| Control | 4.12 | 37.16 | 0.50 | 0.50 | 5.67 | 44.71 | 45.32 |
| 1 μM | 4.89 | 36.45 | 0.56 | 0.62 | 5.05 | 44.13 | 45.78 |
| 2 μM | 4.64 | 33.86 | 0.54 | 0.62 | 5.48 | 46.55 | 42.82 |
| 3 μM | 3.72 | 32.87 | 0.45 | 0.33 | 7.26 | 49.11 | 40.24 |
| 6 μM | 3.99 | 32.92 | 0.52 | 0.44 | 7.05 | 48.45 | 40.78 |
| 9 μM | 4.30 | 30.14 | 0.58 | 0.41 | 7.83 | 49.02 | 38.74 |
| 25 μM | 3.31 | 27.70 | 0.76 | 0.33 | 9.67 | 50.92 | 35.35 |
| 40 μM | 4.02 | 25.60 | 0.91 | 0.35 | 10.93 | 49.62 | 34.88 |

Example 3. Fatty Acid Synthesis Inhibitor Dosing Regimen

Figure 3:
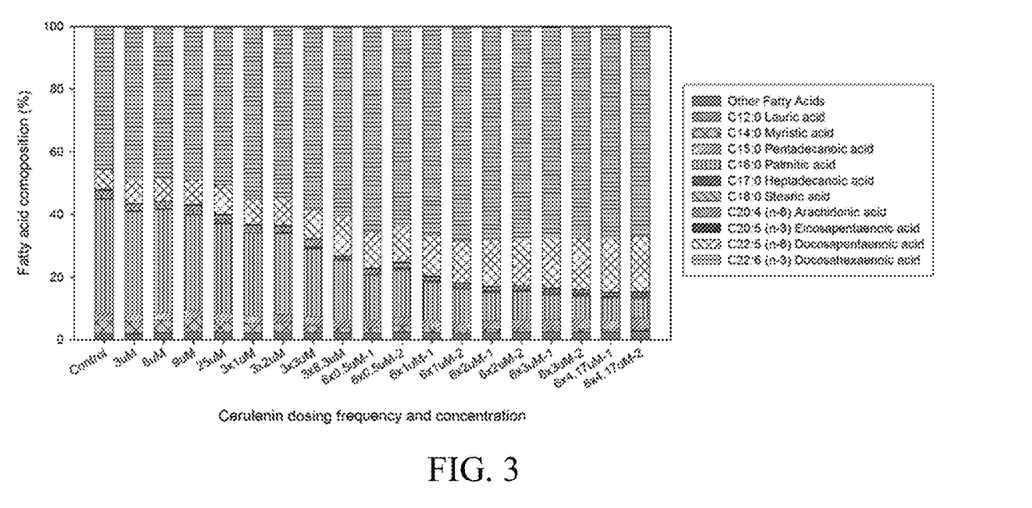
FIG. 3 is a graph showing fatty acid profiles of Aurantiochytrium sp. (G3) in various fatty acid synthesis inhibitor dosing strategies at 20° C. Treatments indicating 3× and 6× are multiple additions of fatty acid synthesis inhibitor at equally-spaced time intervals starting at 24 hours after inoculation. For the 3× experiment, the interval was every 24 hours. For the 6× experiment, the interval was every 12 hours.
Figure 4:
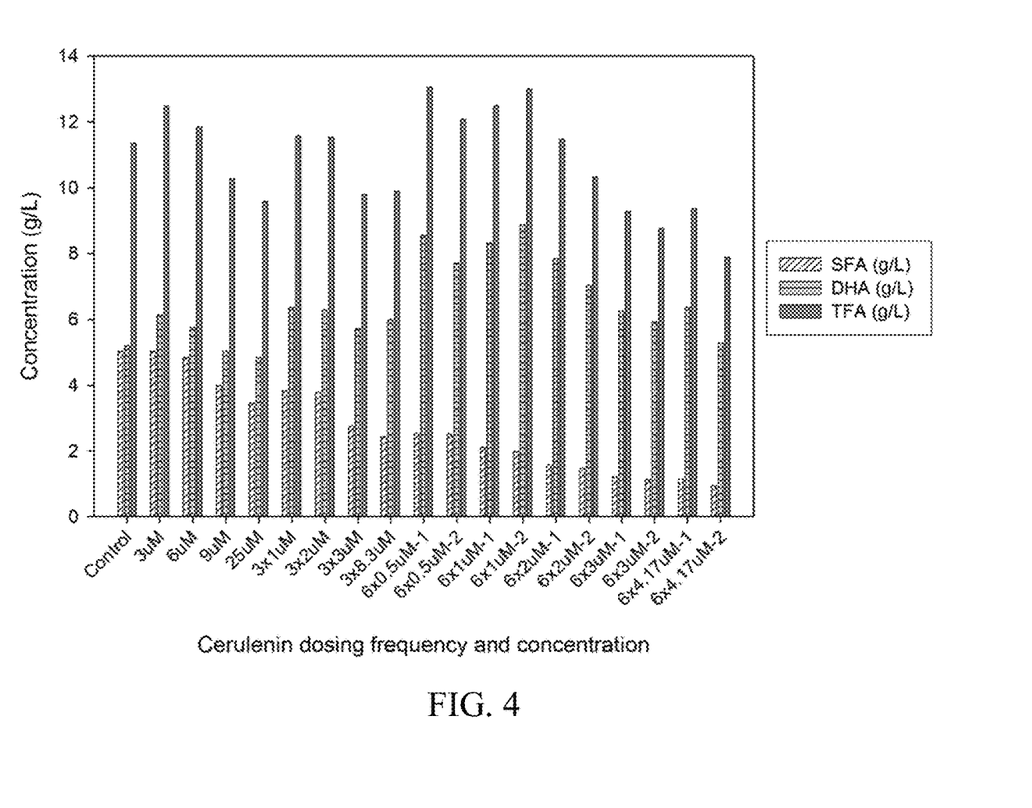
FIG. 4 is a graph showing final product (DHA, total fatty acid (TFA), and saturated fatty acid (SFA)) concentration in Aurantiochytrium sp. (G3) in various fatty acid synthesis inhibitor dosing strategies at 20° C. Treatments indicating 3× and 6× are multiple additions of fatty acid synthesis inhibitor at equally-spaced time intervals (every 12 hours) starting 24 hours after inoculation.

To investigate the effect of prolonged, repeated exposure to cerulenin, doses were spread equally across 3 or 6 times during the experiment. In each case, the total amount added was equivalent to the corresponding treatments that were added entirely at 24 hours. All additions began at 24 hours after inoculation. In FIGS. 3 and 4, a clear trend of increasing DHA and DPA was visible with both increasing cerulenin concentration and by dosing the cerulenin in multiple equivalent pulses. Furthermore, Table 5 shows no negative impact on total fatty acids when repeated dose addition is employed, while the actual amount of DHA (in mg/g) was increasing with increasing cerulenin. The highest DHA observed was using 6 equivalent doses of cerulenin, amounting to 12 μM in total, resulting in a DHA increase of 51.6%. There was also a maximal decrease in C14:0 and C16:0 of 85.1% and 83.9%, suggesting very effective inhibition of the FAS pathway by cerulenin under these conditions.

TABLE 5

Fatty acid content (in mg/g) of *Aurantiochytrium* sp. (G3) in various cerulenin dosing strategies at 20° C. Treatments indicating 3× and 6× are multiple additions of cerulenin at equally-spaced time intervals starting at 24 hours after inoculation. For the 3× addition experiment, the interval was 24 hours; while for the 6× addition experiment, the interval was 12 hours.

Fatty Acid Content (mg/g of dry biomass)

| Cerulenin | C14:0 | C16:0 | C17:0 | C20:5 (n-3) | C22:5 (n-6) | C22:6 (n-3) | SFA | TFA | DHA:DPA |
|---|---|---|---|---|---|---|---|---|---|
| Control | 25.50 | 230.24 | 2.93 | 2.69 | 35.26 | 277.28 | 281.54 | 619.90 | 7.98 |
| 3 μM | 24.49 | 216.49 | 2.95 | 2.15 | 47.79 | 323.48 | 265.09 | 658.72 | 6.77 |
| 6 μM | 24.72 | 204.08 | 3.22 | 2.74 | 43.70 | 300.35 | 252.79 | 619.88 | 6.87 |
| 9 μM | 25.94 | 181.97 | 3.48 | 2.49 | 47.27 | 296.00 | 233.91 | 603.79 | 6.26 |
| 25 μM | 20.09 | 170.38 | 4.36 | 1.90 | 55.73 | 301.00 | 204.48 | 595.96 | 5.40 |
| 3 × 1 μM | 19.42 | 167.92 | 2.66 | 2.35 | 52.40 | 349.67 | 210.60 | 636.22 | 6.67 |
| 3 × 2 μM | 19.58 | 157.98 | 3.14 | 2.54 | 54.90 | 334.67 | 201.30 | 614.40 | 6.10 |
| 3 × 3 μM | 13.28 | 131.13 | 3.40 | 2.34 | 55.54 | 349.04 | 168.66 | 597.67 | 6.28 |
| 3 × 8.3 μM | 9.92 | 117.45 | 3.87 | 1.55 | 78.58 | 373.12 | 151.53 | 617.52 | 4.75 |
| 6 × 0.5 μM | 10.99 | 90.92 | 3.28 | 2.43 | 70.48 | 398.73 | 124.07 | 616.79 | 5.66 |
| 6 × 1 μM | 7.52 | 70.33 | 3.50 | 2.19 | 81.79 | 418.90 | 99.59 | 620.75 | 5.12 |
| 6 × 2 μM | 5.52 | 53.01 | 3.94 | 1.89 | 85.07 | 398.90 | 81.59 | 585.23 | 4.69 |
| 6 × 3 μM | 4.52 | 41.96 | 3.96 | 1.63 | 87.15 | 364.99 | 69.39 | 540.81 | 4.19 |
| 6 × 4.17 μM | 3.79 | 37.13 | 4.14 | 1.56 | 92.73 | 363.03 | 64.00 | 538.56 | 3.91 |

TABLE 6

Fatty acid content (relative to total fatty acids) of *Aurantiochytrium* sp. (G3) in various cerulenin dosing strategies at 20° C. Treatments indicating 3× and 6× are multiple additions of cerulenin at equally-spaced time intervals starting at 24 hours after inoculation. For the 3× addition experiment, the interval was 24 hours; while for the 6× addition experiment, the interval was 12 hours.

Fatty Acid Content (% of TFA)

| Cerulenin | C14:0 | C16:0 | C17:0 | C20:5 (n-3) | C22:5 (n-6) | C22:6 (n-3) | SFA |
|---|---|---|---|---|---|---|---|
| Control | 4.12 | 37.16 | 0.50 | 0.50 | 5.67 | 44.71 | 45.32 |
| 3 μM | 3.72 | 32.87 | 0.45 | 0.33 | 7.26 | 49.11 | 40.24 |
| 6 μM | 3.99 | 32.92 | 0.52 | 0.44 | 7.05 | 48.45 | 40.78 |
| 9 μM | 4.30 | 30.14 | 0.58 | 0.41 | 7.83 | 49.02 | 38.74 |
| 25 μM | 3.37 | 28.59 | 0.76 | 0.33 | 9.35 | 50.51 | 35.35 |
| 3 × 1 μM | 3.05 | 26.39 | 0.42 | 0.37 | 8.24 | 54.96 | 33.10 |
| 3 × 2 μM | 3.19 | 25.71 | 0.51 | 0.41 | 8.93 | 54.47 | 32.76 |
| 3 × 3 μM | 2.22 | 21.94 | 0.57 | 0.39 | 9.29 | 58.40 | 28.22 |
| 3 × 8.3 μM | 1.61 | 19.02 | 0.63 | 0.25 | 12.72 | 60.42 | 24.54 |
| 6 × 0.5 μM | 1.78 | 14.75 | 0.53 | 0.40 | 11.42 | 64.63 | 20.13 |
| 6 × 1 μM | 1.21 | 11.34 | 0.56 | 0.35 | 13.17 | 67.47 | 16.06 |
| 6 × 2 μM | 0.94 | 9.06 | 0.67 | 0.32 | 14.53 | 68.16 | 13.95 |
| 6 × 3 μM | 0.84 | 7.76 | 0.73 | 0.30 | 16.11 | 67.49 | 12.82 |
| 6 × 4.17 μM | 0.70 | 6.88 | 0.77 | 0.29 | 17.23 | 67.39 | 11.88 |

Example 4. Fatty Acid Synthesis Inhibitor Effect on Product Yield

Figure 5:
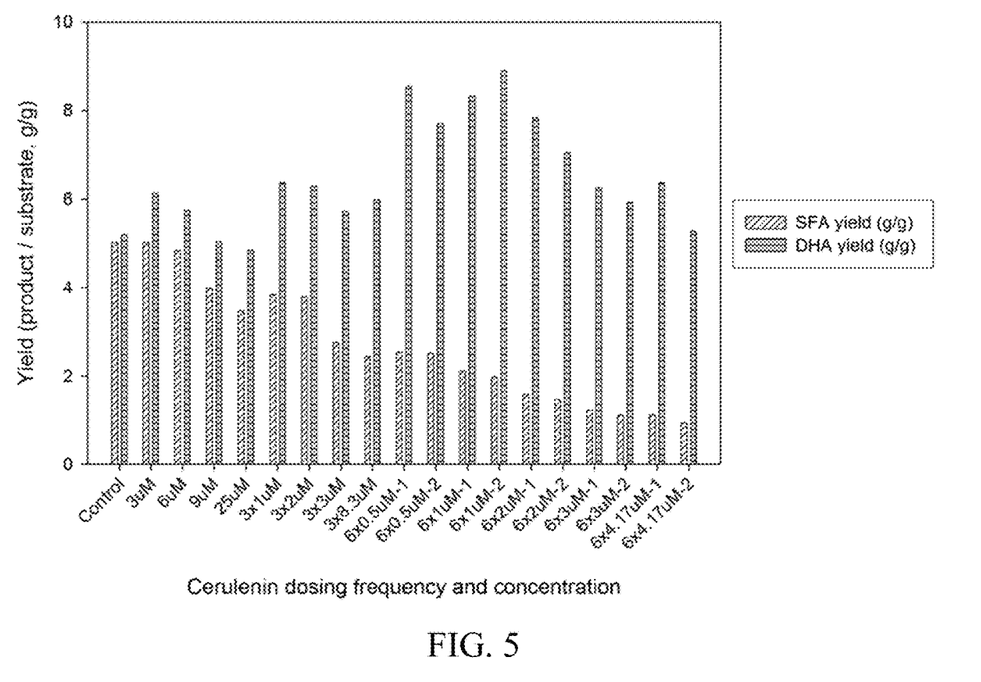
FIG. 5 is a graph showing yield of product (SFA and DHA) per unit of glucose consumed in Aurantiochytrium sp. (G3) in various fatty acid synthesis inhibitor dosing strategies at 20° C. Treatments indicating 3× and 6× are multiple additions of fatty acid synthesis inhibitor at equally-spaced time intervals (every 12 hours) starting at 24 hours after inoculation.

To assess the impact of the herein described methods for PUFA enhancement strategy, the yields of product (i.e. TFA, DHA or DPA) relative to the amount of carbon assimilated by the G3 cells was investigated. In FIG. 5, the total amount of product synthesized (categorized as total fatty acids (TFA), saturated fatty acids (SFA) or DHA) is depicted. In the presence of fatty acid synthesis inhibitors, dosed at certain frequency and concentration, both TFA and DHA concentration increased while SFA concentration decreased. For example, under the condition where cerulenin was dosed 1 μM each time for 6 times at 12 hour intervals, TFA and DHA increased by 15% and 71%, respectively, when compared to the results of the control experiment (FIG. 5). When the results were calculated as fatty acid yield (gram product/ gram carbon consumed), DHA yield generally increased significantly while SFA yield reduced, under any cerulenin dosing conditions. For example, one of the optimal condition at 6×1 μM saw 53% increase in DHA yield and 64% reduction in SFA yield, when compared to the result of the control experiment, thereby suggesting that the cells were not only experiencing inhibition to the FAS pathway but they were up-regulating the PUFA synthase pathway to more efficiently utilize the available carbon.

Example 5. Effects of Temperature on DHA % from Aurantiochytrium sp. (G3)

Figure 6:
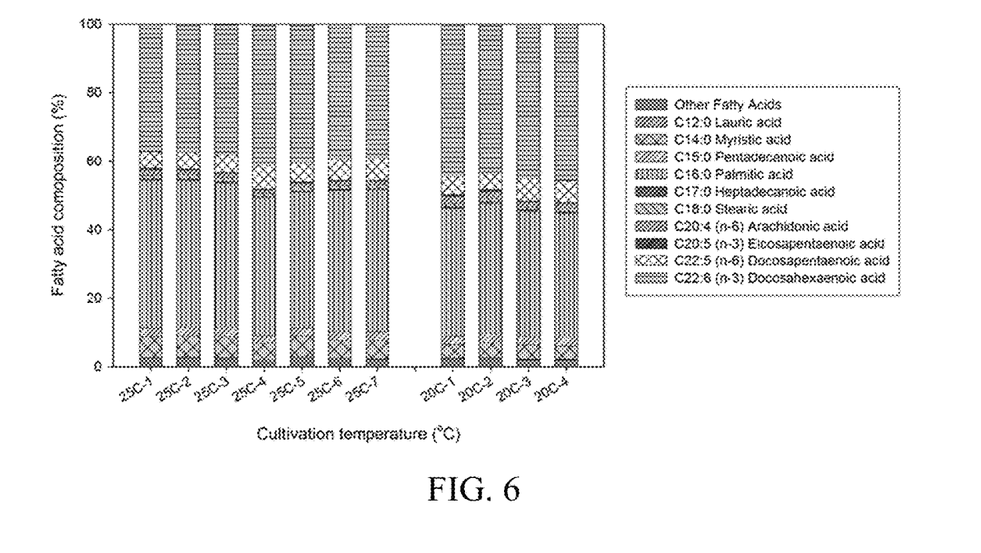
FIG. 6 is a graph showing fatty acid profiles of Aurantiochytrium sp. (G3) from 25° C. and 20° C. cultivation conditions at flask scale.

Flask scale experiments were executed to investigate the impact of decreasing the cultivation temperature (from 25° C. to 20° C.) on the fatty acid profile and the productivity of Aurantiochytrium sp. (G3). The data in FIG. 6 illustrate the increasing proportion of DHA and DPA with a decreased culture temperature to 20° C. Tables 7 and 8 show summary data exhibiting an increase in DHA of 14.7% paired with a decrease in C14:0 and C16:0 by 27.5% and 10.6%, respectively.

TABLE 7

Effect of different temperatures on predominant fatty acids (in mg/g) and their relationships present in *Aurantiochytrium* sp. (G3)

Fatty Acid Content (mg/g of dry biomass)

| | C14:0 | C16:0 | C17:0 | C20:5 (n-3) | C22:5 (n-6) | C22:6 (n-3) | SFA | TFA | DHA:DPA |
|---|---|---|---|---|---|---|---|---|---|
| 25° C. | 35.73 | 262.05 | 2.58 | 2.59 | 35.68 | 246.18 | 324.31 | 630.78 | 7.03 |
| 20° C. | 25.50 | 230.24 | 3.07 | 3.10 | 35.26 | 277.28 | 280.75 | 619.90 | 7.98 |

TABLE 8

Effect of different temperatures on predominant fatty acids
(relative to total fatty acids) present in Aurantiochytrium sp. (G3).
Fatty Acid Content (% of TFA)

|  | C14:0 | C16:0 | C17:0 | C20:5 (n-3) | C22:5 (n-6) | C22:6 (n-3) | SFA |
|---|---|---|---|---|---|---|---|
| 25° C. | 5.68 | 41.57 | 0.41 | 0.41 | 5.64 | 38.99 | 51.46 |
| 20° C. | 4.12 | 37.16 | 0.50 | 0.50 | 5.67 | 44.71 | 45.32 |

Example 6. Effects of Full-length Fermentation on DHA % from Aurantiochytrium sp. (G3)

Figure 7:
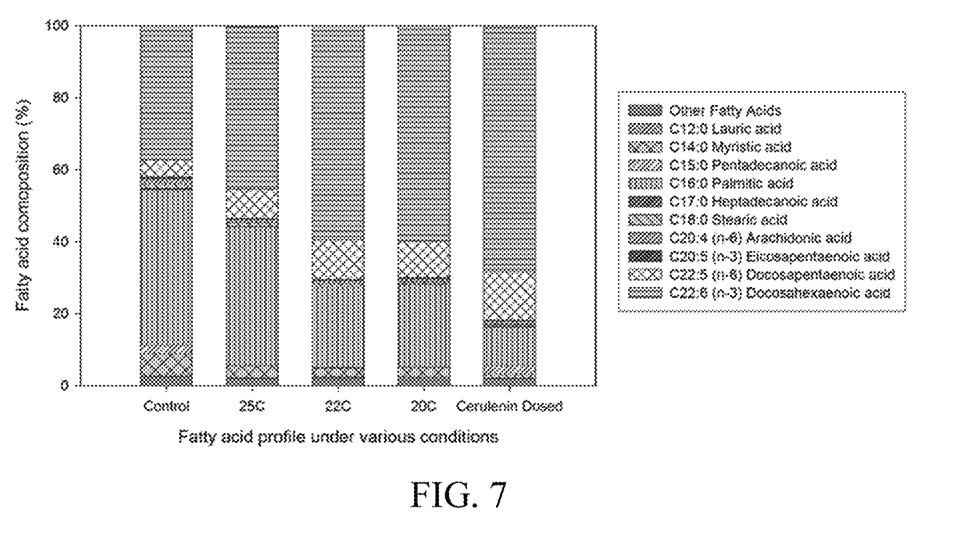
FIG. 7 is a graph showing the fatty acid profiles of Aurantiochytrium sp. (G3). Controls were cultured in flask at 25° C. with no chemical inhibitor. The full-length fermentation runs were fed-batch fermentations in 30 L fermentor at the noted temperature, and the fatty acid synthesis inhibitor treatment was cultured at 20° C. with a pulsed addition of 12 µM total cerulenin at flask scale.

Full-length fermentations of Aurantiochytrium sp. G3 were carried out using 30 L stainless steel fermentors at varying temperatures (from 25° C. to 20° C.). These fermentations generally lasted from 150 hours to 200 hours with biomass and TFA reaching over 130 g/L and 55%, respectively. As can be seen in FIG. 7, full-length fermentation at a typical temperature of 25° C. was able to improve final DHA content over that from a typical control cultivation using flask; while full-length fermentations at lower temperatures were able to reach even higher DHA %. In the examples included in FIG. 7, fermentation at 25° C. reached 45% DHA, about 8% higher than that of a flask control at 37%. Fermentations at 22° C. and 20° C. achieved further DHA % increase at 59.7% and 60.0%, respectively. However, DHA content from the flask experiment using multiple and intermittent dosing of cerulenin was still the highest DHA % reached, at 68.7%.

Example 7. Effects of Elevated Temperature on Aurantiochytrium sp. (G3)

G3 strains were cultured in 30-L fermenters for enhanced biomass and fatty acid production at 22° C., 25° C., and 28° C. G3 was pre-cultured in four Erlenmeyer flasks containing 500 mL of basal media (50 g/L glucose, 6.25 g/L yeast extract, 4 g/L MgSO$_4$7H$_2$O, 4 g/L, 2.5 g/L NaCl, 2 mg/L copper sulfate, 2 mg/L zinc sulfate, 1 mg/L sodium molybdate, 1 mg/L cobalt (II) chloride, 1 mg/L manganese chloride and 1 mg/L nickel sulfate). Flasks were incubated under agitation at 25° C. and 200 rpm for 2 days. After the incubation period, three of the flasks (1.5 L) were used to inoculate 20 L of media in a 30 L bioreactor containing 175 g/L glucose, 9.66 g/L yeast extract, 2.57 g/L MgSO$_4$7H$_2$O, 0.45 g/L sodium chloride, 6.44 g/L ammonium sulfate, 1.6 g/L potassium phosphate monobasic, 1.74 g/L potassium phosphate dibasic, 12.87 g/L monosodium glutamate, 0.1 g/L calcium chloride dehydrate, 1 mg/L copper sulfate, 1 mg/L zinc sulfate, 0.5 mg/L sodium molybdate, 0.5 mg/L cobalt (II) chloride, 0.5 mg/L manganese chloride, 0.5 mg/L nickel sulfate, 0.03 mg/L vitamin B12, 0.03 mg/L biotin and 6 mg/L thiamin hydrochloride and cultured in 30-L fermenters under the conditions of 22° C., 25° C., and 28° C. Agitation started at 325 rpm and increased to 365 rpm, aeration was maintained at 0.3 vvm with atmospheric air, and pH 6.0. pH was maintained by the addition of base (27% NH$_4$OH). Vessels were fed to maintain a glucose consumption rate of approximately 3 g/L/h with a 750 g/L glucose solution. Cells were collected at various intervals and the biomass, TFA and lipid profiles were measured. Characteristics of the final G3 profiles at 25 and 28° C. are shown in Table 9. The lipid profiles are shown in Tables 10, 11, and 12.

TABLE 9

G3 Final Results at 22, 25 and 28° C.

|  | G3 at 22° C. | G3 at 25° C. | G3 at 28° C. |
|---|---|---|---|
| Time, h | 186.89 | 140.19 | 165.67 |
| Biomass, g/L | 121.83 | 107.92 | 104.16 |
| TFA, % biomass | 49.6 | 56.3 | 59.2 |
| DHA, % TFA | 66.78 | 64.1 | 58.6 |
| SFA, % TFA | 16.18 | 19 | 25 |
| MUFA, % TFA |  | 0.9 | 0.8 |

TABLE 10

Fatty Acid Profile of G3 Cultured at 22° C.

| Lipid: | 12:0 | 14:0 | 14:1 | 15:0 | 16:0 | 16:1 | 18:0 | 18:1 Vac | 20:0 | 20:4 (n-6) | 20:5 (n-3) EPA | 22:0 | 22:5 (n-6) DPA | C22:5 (n-3) DPA* | C22:6 (n-3) DHA* |
|---|---|---|---|---|---|---|---|---|---|---|---|---|---|---|---|
| 45 h | 0.06 | 0.96 | 0.24 | 0.34 | 24.64 | 0.16 | 1.10 | 0.32 | 0.12 | 0.65 | 0.50 | 0.24 | 9.44 | 0.24 | 58.47 |
| 68 h | 0.08 | 1.35 | 0.29 | 0.24 | 21.17 | 0.23 | 0.86 | 0.39 | 0.14 | 0.65 | 0.38 | 0.16 | 10.25 | 0.16 | 61.51 |
| 90 h | 0.08 | 1.30 | 0.47 | 0.20 | 17.12 | 0.32 | 0.68 | 0.38 | 0.17 | 0.89 | 0.39 | 0.17 | 10.61 | 0.13 | 65.25 |
| 115 h | 0.08 | 1.17 | 0.63 | 0.12 | 14.17 | 0.38 | 0.53 | 0.37 | 0.16 | 1.08 | 0.42 | 0.14 | 10.91 | 0.12 | 68.07 |
| 141 h | 0.08 | 1.06 | 0.71 | 0.10 | 13.21 | 0.41 | 0.49 | 0.40 | 0.15 | 1.15 | 0.44 | 0.14 | 11.57 | 0.13 | 68.22 |
| 163 h | 0.08 | 1.11 | 0.66 | 0.10 | 13.71 | 0.40 | 0.51 | 0.41 | 0.15 | 1.08 | 0.46 | 0.14 | 11.80 | 0.14 | 67.50 |
| 187 h | 0.08 | 1.11 | 0.62 | 0.09 | 14.32 | 0.37 | 0.52 | 0.43 | 0.15 | 1.02 | 0.47 | 0.15 | 12.02 | 0.15 | 66.69 |

TABLE 11

Fatty Acid Profile of G3 Cultured at 25° C.

| Lipid: | 12:0 | 14:0 | 14:1 | 15:0 | 16:0 | 16:1 | 18:0 | 18:1 Vac | 20:0 | 20:4 (n-6) | 20:5 (n-3) EPA | 22:0 | 22:5 (n-6) DPA | C22:5 (n-3) DPA* | C22:6 (n-3) DHA* |
|---|---|---|---|---|---|---|---|---|---|---|---|---|---|---|---|
| 63 h | 0.11 | 1.07 | 0.23 | 0.21 | 20.93 | 0.16 | 0.83 | 0.17 | 0.14 | 0.54 | 0.33 | 0.12 | 12.02 | 0.16 | 60.79 |
| 92 h | 0.15 | 1.29 | 0.35 | 0.17 | 19.66 | 0.22 | 0.78 | 0.19 | 0.16 | 0.62 | 0.29 | 0.17 | 12.00 | 0.12 | 60.78 |
| 116 h | 0.08 | 1.19 | 0.49 | 0.12 | 16.18 | 0.25 | 0.59 | 0.19 | 0.15 | 0.81 | 0.33 | 0.12 | 12.94 | 0.12 | 64.60 |
| 140 h | 0.08 | 1.22 | 0.43 | 0.11 | 16.85 | 0.25 | 0.56 | 0.21 | 0.13 | 0.7 | 0.35 | 0.10 | 12.99 | 0.14 | 64.13 |

TABLE 12

Fatty Acid Profile of G3 Cultured at 28° C.

| Lipid | 12:0 | 14:0 | 14:1* | 15:0 | 16:0 | 16:1 | 18:0 | 18:1 Vac | 20:0 | 20:4 (n-6) | 20:5 (n-3) EPA | 22:0 | 22:5 (n-6) DPA | C22:5 (n-3) DPA* | C22:6 (n-3) DHA* |
|---|---|---|---|---|---|---|---|---|---|---|---|---|---|---|---|
| 63 h | 0.10 | 1.24 | 0.22 | 0.21 | 19.28 | 0.16 | 0.71 | 0.13 | 0.13 | 0.50 | 0.32 | 0.12 | 13.66 | 0.19 | 60.76 |
| 92 h | 0.12 | 1.26 | 0.26 | 0.17 | 17.29 | 0.18 | 0.61 | 0.14 | 0.15 | 0.49 | 0.28 | 0.12 | 14.47 | 0.20 | 62.22 |
| 116 h | 0.13 | 1.41 | 0.40 | 0.16 | 18.75 | 0.23 | 0.65 | 0.20 | 0.15 | 0.68 | 0.30 | 0.11 | 13.67 | 0.16 | 61.10 |
| 140 h | 0.08 | 1.60 | 0.39 | 0.15 | 21.05 | 0.25 | 0.67 | 0.23 | 0.12 | 0.74 | 0.33 | 0.10 | 13.02 | 0.15 | 59.36 |
| 166 | 0.09 | 1.66 | 0.31 | 0.14 | 22.10 | 0.23 | 0.66 | 0.22 | 0.10 | 0.75 | 0.44 | 0.08 | 12.84 | 0.16 | 58.55 |

What is claimed is:

1. An Aurantiochytrium microalgal oil comprising at least 85% total fatty acids by weight, wherein the total fatty acids comprise at least 45% docosahexaenoic acid by weight, and between 6% to 18% docosapentaenoic acid n-6 by weight, and wherein the ratio of docosahexaenoic acid to docosapentaenoic acid n-6 is between 3:1 and 7:1, and wherein the microalgal oil is produced by a microorganism having International Depositary Authority of Canada Accession No. 220716-01.

2. An Aurantiochytrium microalgal oil comprising at least 85% total fatty acids by weight, wherein the total fatty acids comprise at least 45% docosahexaenoic acid by weight, 0.01% to 1% stearic acid by weight, 6% to 18% docosapentaenoic acid n-6 by weight, 0.001% to 5% myristic acid by weight, 10% to 30% palmitic acid by weight, 0.001% to 0.5% heptadecanoic acid by weight, and 0.001% to 2% of arachidonic acid by weight, wherein the microalgal oil is produced by a microorganism having International Depositary Authority of Canada Accession No. 220716-01.

3. The microalgal oil of claim 1, wherein the total fatty acids comprise one or more of 0.001% to 2% eicosapentaenoic acid by weight and 0.001% to 3% pentadecanoic acid by weight.

4. The microalgal oil of claim 1, wherein the total fatty acids comprise between 15% and 45% saturated fatty acids.

5. The microalgal oil of claim 1, wherein the total fatty acids comprise one or more of 60% to 70% docosahexaenoic acid by weight, 0.001% to 2.0% arachidonic acid by weight, and 0.01% to 1% eicosatetraenoic acid by weight.

6. The microalgal oil of claim 1, wherein the microalgal oil comprises at least 90% triglycerides.

7. The microalgal of claim 2, wherein the total fatty acids comprise one or more of 0.001% to 2% eicosapentaenoic acid by weight and 0.001% to 3% pentadecanoic acid by weight.

8. The microalgal of claim 2, wherein the total fatty acids comprise between 15% and 45% saturated fatty acids.

9. The microalgal of claim 2, wherein the total fatty acids comprise 60% to 70% docosahexaenoic acid by weight and 0.01% to 1% eicosatetraenoic acid by weight.

10. The microalgal of claim 2, wherein the microalgal oil comprises at least 90% triglycerides.

11. The microalgal of claim 2, wherein the ratio of docosahexaenoic acid to docosapentaenoic acid n-6 is between 3:1 and 7:1.

* * * * *